(12) United States Patent
Pacella et al.

(10) Patent No.: US 11,793,863 B2
(45) Date of Patent: Oct. 24, 2023

(54) FUNCTIONALIZED MICROBUBBLE EMBODIMENTS FOR ULTRASOUND-MEDIATED TREATMENT AND METHODS OF MAKING AND USING THE SAME

(71) Applicants: University of Pittsburgh—Of the Commonwealth System of Higher Education, Pittsburgh, PA (US); UPMC, Pittsburgh, PA (US)

(72) Inventors: John J. Pacella, Pittsburgh, PA (US); Xucai Chen, Pittsburgh, PA (US); Francois Tchi Ho Yu, Montreal (CA); Thiruganesh Ramasamy, Pittsburgh, PA (US); Stephen D'Auria, West View, PA (US)

(73) Assignees: University of Pittsburgh—Of the Commonwealth System of Higher Education, Pittsburgh, PA (US); UPMC, Pittsburgh, PA (US)

(*) Notice: Subject to any disclaimer, the term of this patent is extended or adjusted under 35 U.S.C. 154(b) by 560 days.

(21) Appl. No.: 16/858,383

(22) Filed: Apr. 24, 2020

(65) Prior Publication Data

US 2020/0338172 A1 Oct. 29, 2020

Related U.S. Application Data

(60) Provisional application No. 62/839,490, filed on Apr. 26, 2019.

(51) Int. Cl.
| | | |
|---|---|---|
| *A61K 38/48* | (2006.01) | |
| *A61K 9/16* | (2006.01) | |
| *A61K 47/54* | (2017.01) | |
| *A61P 9/14* | (2006.01) | |
| *A61K 45/06* | (2006.01) | |
| *A61K 9/00* | (2006.01) | |
| *A61K 41/00* | (2020.01) | |
| *A61K 47/64* | (2017.01) | |

(52) U.S. Cl.
CPC .......... *A61K 38/482* (2013.01); *A61K 9/0019* (2013.01); *A61K 9/1617* (2013.01); *A61K 41/0047* (2013.01); *A61K 45/06* (2013.01); *A61K 47/545* (2017.08); *A61K 47/64* (2017.08); *A61P 9/14* (2018.01)

(58) Field of Classification Search
CPC ..... A61K 38/482; A61K 9/1617; A61K 47/64
See application file for complete search history.

(56) References Cited

U.S. PATENT DOCUMENTS

| | | |
|---|---|---|
| 5,558,092 A | 9/1996 | Unger et al. |
| 5,695,460 A | 12/1997 | Siegel et al. |
| 2005/0084538 A1 | 4/2005 | Dayton et al. |
| 2006/0264809 A1 | 11/2006 | Hansmann et al. |
| 2008/0319375 A1 | 12/2008 | Hardy |
| 2010/0143241 A1 | 6/2010 | Johnson et al. |
| 2011/0201974 A1 | 8/2011 | Soltani et al. |
| 2015/0141817 A1 | 5/2015 | Chen et al. |
| 2016/0106866 A1* | 4/2016 | Fisher ................ A61K 49/0054 424/9.1 |

FOREIGN PATENT DOCUMENTS

| | | |
|---|---|---|
| WO | WO 1999/042138 | 8/1999 |
| WO | WO 2008/017997 | 2/2008 |
| WO | WO 2014/004912 | 1/2014 |

OTHER PUBLICATIONS

Pu et al., Mol. Pharma. 11: 49-58, (2014).*
Bekeredjian et al. "Use of Ultrasound Contrast Agents for Gene or Drug Delivery in Cardiovascular Medicine," *Journal of the American College of Cardiology* 45 (2005): 329-335.
Choi et al., "Noninvasive and localized blood-brain barrier disruption using focused ultrasound can be achieved at short pulse lengths and low pulse repetition frequencies," *Journal of Cerebral Blood Flow & Metabolism* 31 (2011): 725-737.
D'Auria et al. "Development of a Unique Tissue Plasminogen Activator (tPA) loaded Microbubble for the Treatment of Coronary Microvascular Obstruction" Poster Presentation, May 1, 2018.
Datta et al. "Correlation of cavitation with ultrasound enhancement of thrombolysis." *Ultrasound in medicine & biology* 32 (2006): 1257-1267.
Datta et al. "Ultrasound-Enhanced Thrombolysis Using Definity<sup>®</sup> as a Cavitation Nucleation Agent." *Ultrasound in medicine & biology* 34 (2008): 1421-1433.
Forbes et al., "Examination of Inertial Cavitation of Optison™ in Producing Sonoporation of Chinese Hamster Ovary Cells." *Ultrasound in Medicine and Biology* 34 (2008): 2009-2018.
Goertz et al. "Contrast Agent Kinetics in the Rabbit Brain During Exposure to Therapeutic Ultrasound," *Ultrasound in Medicine and Biology* 36 (2010): 916-924.
Hua et al., "Construction of thrombus-targeted microbubbles carrying tissue plasminogen activator and their in vitro thrombolysis efficacy: a primary research," *J Thromb Thrombolysis*, vol. 30, pp. 29-35, Feb. 14, 2010.
Hua et al., "In vivo thrombolysis with targeted microbubbles loading tissue plasminogen activator in a rabbit femoral artery thrombus model," *J Thromb Thrombolysis*, vol. 38, pp. 57-64, Mar. 27, 2014.

(Continued)

*Primary Examiner* — Gyan Chandra
(74) *Attorney, Agent, or Firm* — Klarquist Sparkman, LLP

(57) ABSTRACT

Disclosed herein are embodiments of a functionalized microbubble designed for treating and/or preventing vascular obstructions, including microvascular obstructions. The functionalized microbubble embodiments comprise a microbubble that can be activated upon exposure to ultrasound and further that has a lipid-based shell that is attached to an exteriorly-attached therapeutically active agent, such as a thrombolytic agent. Also disclosed herein are embodiments of a method for making and using the functionalized microbubble embodiments.

22 Claims, 8 Drawing Sheets

(56) References Cited

OTHER PUBLICATIONS

Ito et al. "Clinical Implications of the 'No Reflow' Phenomenon: a Predictor of Complications and Left Ventricular Remodeling in Reperfused Anterior Wall Myocardial Infarction," *Circulation* 93.2 (1996): 223-228.

Kutty et al. "Sonothrombolysis of intra-catheter aged venous thrombi using microbubble enhancement and guided three-dimensional ultrasound pulses." *Journal of the American Society of Echocardiography* 23 (2010): 1001-1006.

Laing et al. "Thrombolytic efficacy of tissue plasminogen activator-loaded echogenic liposomes in a rabbit thrombus model." *Thrombosis Research* 130.4 (2012): 629-635.

Leeman et al. "Effect of acoustic conditions on microbubble-mediated microvascular sonothrombolysis." *Ultrasound in medicine & biology* 38.9 (2012): 1589-1598.

Lentacker et al. "Drug loaded microbubble design for ultrasound triggered delivery," *Soft Matter* 5.11 (2009): 2161-2170.

Nedelmann et al. "Combined contrast-enhanced ultrasound and rt-PA treatment is safe and improves impaired microcirculation after reperfusion of middle cerebral artery occlusion." *Journal of Cerebral Blood Flow & Metabolism* 30 (2010): 1712-1720.

O'Reilly et al. Focused-Ultrasound Disruption of the Blood-Brain Barrier Using Closely-Timed Short Pulses: Influence of Sonication Parameters and Injection Rate, *Ultrasound in Medicine and Biology* 37 (2011): 587-594.

Pacella et al. "Treatment of microvascular micro-embolization using microbubbles and long-tone-burst ultrasound: an in vivo study." *Ultrasound in Medicine & Biology* 41.2 (2015): 456-464.

Prokop et al. "Cavitational mechanisms in ultrasound-accelerated fibrinolysis." *Ultrasound in medicine & biology* 33 (2007): 924-933. (Abstract only).

Sen et al. "Mechanical index." *Anatolian Journal of Cardiology*, 15(4): 334-336, Apr. 2015.

Sorace et al., "Microbubble-mediated ultrasonic techniques for improved chemotherapeutic delivery in cancer," *Journal Drug Target* 20 (2012): 43-54.

Teupe et al. "Vascular Gene Transfer of Phosphomimetic Endothelial Nitric Oxide Synthase (S1177D) Using Ultrasound-Enhanced Destruction of Plasmid-Loaded Microbubbles Improves Vasoreactivity," *Circulation* 105 (2002): 1104-1109.

Tiukinhoy-Laing et al. "Ultrasound-facilitated thrombolysis using tissue-plasminogen activator-loaded echogenic liposomes," *Thrombosis Research* 119 (2007): 777-784.

Tung et al. "The mechanism of interaction between focused ultrasound and microbubbles in blood-brain barrier opening in mice," *Journal of the Acoustic Society of America* 130 (2011): 3059-3067.

Wilkens et al. "Output intensity measurement on a diagnostic ultrasound machine using a calibrated thermoacoustic sensor." *Journal of Physics: Conference Series, Advanced Metrology for Ultrasound in Medicine*, 1(1): 140-145, Jan. 1, 2004.

Xie et al. "Diagnostic ultrasound combined with glycoprotein IIb/IIIa-targeted microbubbles improves microvascular recovery after acute coronary thrombotic occlusions." *Circulation* 119 (2009): 1378-1385.

Yan et al., "Fabrication of ultrasound-responsive microbubbles via coaxial electrohydrodynamic atomization for triggered release of tPA," *Journal of Colloid and Interface Science*, vol. 501, pp. 282-293, Apr. 24, 2017.

* cited by examiner

Concentration of tPA on tPA loaded Microbubbles

*p < 0.0001 vs time = 0
**p < 0.05 vs tMB

*p < 0.0001 vs time = 0
**p < 0.05 vs tMB

FUNCTIONALIZED MICROBUBBLE EMBODIMENTS FOR ULTRASOUND-MEDIATED TREATMENT AND METHODS OF MAKING AND USING THE SAME

CROSS-REFERENCE TO RELATED APPLICATION

This application claims the benefit of the earlier filing date of U.S. Provisional Application No. 62/839,490, filed on Apr. 26, 2019, which is incorporated herein by reference in its entirety.

FIELD

Disclosed herein are embodiments of microbubbles externally labeled with an active agent, such as tissue plasminogen activator (tPA), and methods of making and using the same to treat microvascular obstructions.

BACKGROUND

Microvascular obstruction (MVO) occurs frequently during successful percutaneous coronary intervention (PCI) for acute myocardial infarction (AMI). MVO limits myocardial salvage and is the primary contributor to post AMI congestive heart failure. Due to decreased NO bioavailability, patients with AMI have reduced endogenous tissue plasminogen activator (tPA) release. Systemic tPA is an established therapy for AMI when PCI is unavailable. However, it creates a systemic lytic state leading to bleeding complications, even when used at low dose; therefore, post PCI administration of systemic tPA is not a viable approach to treating MVO. Conventional techniques of using tPA for therapeutic purposes have significant limitations and, as such, improved methods and systems for providing tPA to subjects are needed in the art.

SUMMARY

Disclosed herein are embodiments of a functionalized microbubble. In some embodiments, the microbubble comprises: a microbubble comprising a lipid-based shell, wherein the lipid-based shell comprises (i) an interior circumferential region that defines a core of the microbubble and (ii) an exterior circumferential region; and at least one exteriorly-positioned thrombolytic agent attached to the exterior circumferential region of the lipid-based shell; wherein the at least one exteriorly-positioned thrombolytic agent extends from the exterior circumferential region and away from the core.

Also disclosed herein are embodiments of a therapeutic composition, comprising: a functionalized microbubble; and a pharmaceutically acceptable excipient, one or more additional therapeutically active agents or visualization agents, or any combinations thereof. In some embodiments, the therapeutic composition further comprises a microbubble that is not functionalized with a thrombolytic agent.

Also disclosed herein are embodiments of a method, comprising: exposing a subject or a sample to the functionalized microbubble of any one or more of the above embodiments, or the therapeutic composition of any one or more of the above therapeutic composition embodiments; and applying an ultrasound tone burst within a vicinity of the functionalized microbubble.

Also disclosed herein are embodiments of a method for treating a microvascular obstruction in a microvascular structure, comprising: exposing a subject or a sample to the functionalized microbubble of any one or more of the above embodiments, or the therapeutic composition of any one or more of the above therapeutic composition embodiments; visualizing the functionalized microbubble in the subject or the sample after exposure; applying one or more tone bursts of ultrasound within a vicinity of the functionalized microbubble once the functionalized microbubble is in proximity of a thrombus; and reducing a size of the thrombus to a size sufficient to remove the microvascular obstruction and allow blood flow to continue through the microvascular structure.

The foregoing and other objects and features of the present disclosure will become more apparent from the following detailed description, which proceeds with reference to the accompanying figures.

BRIEF DESCRIPTION OF THE DRAWINGS

FIGS. 4A and 4B show results for tPA only (top rows), a tPA-functionalized microbubble embodiment (middle rows), and pre burst tPA-functionalized microbubble embodiments (bottom rows) before (FIG. 4A) and after (FIG. 4B) 24 hours; FIGS. 4C and 4D show a buffered control solution of the thrombus before (FIG. 4C) and after (FIG. 4D) 24 hours.

DETAILED DESCRIPTION

Overview of Terms

Figure 1:
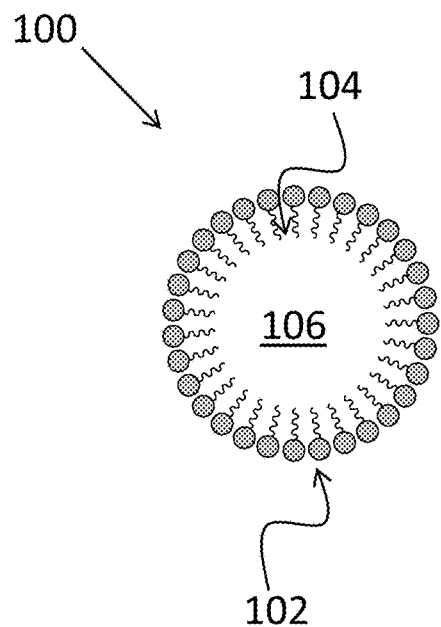
FIG. 1 is an illustration of a representative microbubble component that can be used for the functionalized microbubble embodiments disclosed herein.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided. Certain functional group terms include a symbol "—" which is used to show how the defined functional group attaches to, or within, the compound to which it is bound. A person of ordinary skill in the art would recognize that the definitions provided below and the compounds and formulas included herein are not intended to include impermissible substitution patterns (e.g., methyl substituted with 5 different groups, and the like). Such impermissible substitution patterns are easily recognized by a person of ordinary skill in the art. In formulas and compounds disclosed herein, a hydrogen atom is present and completes any formal valency requirements (but may not necessarily be illustrated) wherever a functional group or other atom is not illustrated. For example, a phenyl ring that is drawn as

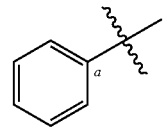

comprises a hydrogen atom attached to each carbon atom of the phenyl ring other than the "a" carbon, even though such hydrogen atoms are not illustrated. Any functional group disclosed herein and/or defined above can be substituted or unsubstituted, unless otherwise indicated herein.

Acyl Halide: —C(O)X, wherein X is a halogen, such as Br, F, I, or Cl.

Aldehyde: —C(O)H.

Aliphatic: A hydrocarbon group having at least one carbon atom to 50 carbon atoms ($C_{1-50}$), such as one to 25 carbon atoms ($C_{1-25}$), or one to ten carbon atoms ($C_{1-10}$), and which includes alkanes (or alkyl), alkenes (or alkenyl), alkynes (or alkynyl), including cyclic versions thereof, and further including straight- and branched-chain arrangements, and all stereo and position isomers as well. Cyclic aliphatic groups comprising alkenes are distinct from aromatic groups.

Aliphatic-aromatic: An aromatic group that is or can be coupled to a compound disclosed herein, wherein the aromatic group is or becomes coupled through an aliphatic group.

Aliphatic-aryl: An aryl group that is or can be coupled to a compound disclosed herein, wherein the aryl group is or becomes coupled through an aliphatic group.

Aliphatic-heteroaryl: A heteroaryl group that is or can be coupled to a compound disclosed herein, wherein the heteroaryl group is or becomes coupled through an aliphatic group.

Alkenyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z). Cyclic alkenyl groups are distinct from aromatic groups.

Alkoxy: —O-aliphatic, such as —O-alkyl, —O-alkenyl, —O-alkynyl; with exemplary embodiments including, but not limited to, methoxy, ethoxy, n-propoxy, isopropoxy, n-butoxy, t-butoxy, sec-butoxy, n-pentoxy (wherein any of the aliphatic components of such groups can comprise no double or triple bonds, or can comprise one or more double and/or triple bonds).

Alkyl: A saturated monovalent hydrocarbon having at least one carbon atom to 50 carbon atoms ($C_{1-50}$), such as one to 25 carbon atoms ($C_{1-25}$), or one to ten carbon atoms ($C_{1-10}$), wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkynyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Amide: —C(O)NR$^a$R$^b$ or —NR$^a$C(O)R$^b$ wherein each of R$^a$ and R$^b$ independently is selected from hydrogen, aliphatic, heteroaliphatic, haloaliphatic, haloheteroaliphatic, aromatic, or an organic functional group.

Amino: —NR$^a$R$^b$, wherein each of R$^a$ and R$^b$ independently is selected from hydrogen, aliphatic, heteroaliphatic, haloaliphatic, haloheteroaliphatic, aromatic, or an organic functional group.

Aromatic: A cyclic, conjugated group or moiety of, unless specified otherwise, from 5 to 15 ring atoms having a single ring (e.g., phenyl) or multiple condensed rings in which at least one ring is aromatic (e.g., naphthyl, indolyl, or pyrazolopyridinyl); that is, at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example, However, in certain examples, context or express disclosure may indicate that the point of attachment is through a non-aromatic portion of the condensed ring system. For example, An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety. Aromatic groups may be substituted with one or more groups other than hydrogen, such as aliphatic, heteroaliphatic, haloaliphatic, haloheteroaliphatic, aromatic, or an organic functional group.

Aryl: An aromatic carbocyclic group comprising at least five carbon atoms to 15 carbon atoms ($C_5$-$C_{15}$), such as five to ten carbon atoms ($C_5$-$C_{10}$), having a single ring or multiple condensed rings, which condensed rings can or may not be aromatic provided that the point of attachment to a remaining position of the compounds disclosed herein is through an atom of the aromatic carbocyclic group. Aryl groups may be substituted with one or more groups other than hydrogen, such as aliphatic, heteroaliphatic, haloaliphatic, haloheteroaliphatic, aromatic, or an organic functional group.

Aroxy: —O-aromatic.

Azo: —N=NR$^a$ wherein R$^a$ is hydrogen, aliphatic, heteroaliphatic, haloaliphatic, haloheteroaliphatic, aromatic, or an organic functional group.

Carbamate: —OC(O)NR$^a$R$^b$, wherein each of R$^a$ and R$^b$ independently is selected from hydrogen, aliphatic, heteroaliphatic, haloaliphatic, haloheteroaliphatic, aromatic, or an organic functional group.

Carboxyl: —C(O)OH.

Carboxylate: —C(O)O$^-$ or salts thereof, wherein the negative charge of the carboxylate group may be balanced with an M$^+$ counterion, wherein M$^+$ may be an alkali ion, such as K$^+$, Na$^+$, Li$^+$; an ammonium ion, such as +N(R$^b$)$_4$ where R$^b$ is H, aliphatic, heteroaliphatic, haloaliphatic, haloheteroaliphatic, or aromatic; or an alkaline earth ion, such as [Ca$^{2+}$]$_{0.5}$, [Mg$^{2+}$]$_{0.5}$, or [Ba$^{2+}$]$_{0.5}$.

Covalent Binding Partner: A functional group (e.g., an organic functional group) capable of forming a covalent chemical bond with another covalent binding partner.

Cyano: —CN.

Disulfide: —SSR$^a$, wherein R$^a$ is selected from hydrogen, aliphatic, heteroaliphatic, haloaliphatic, haloheteroaliphatic, aromatic, or an organic functional group.

Dithiocarboxylic: —C(S)SR$^a$ wherein R$^a$ is selected from hydrogen, aliphatic, heteroaliphatic, haloaliphatic, haloheteroaliphatic, aromatic, or an organic functional group.

Ester: —C(O)OR$^a$ or —OC(O)R$^a$, wherein R$^a$ is selected from aliphatic, heteroaliphatic, haloaliphatic, haloheteroaliphatic, aromatic, or an organic functional group.

Ether: -aliphatic-O-aliphatic, -aliphatic-O-aromatic, -aromatic-O-aliphatic, or -aromatic-O-aromatic.

Exterior Circumferential Region: A region of a lipid-based shell of a microbubble embodiment that defines the exterior surface of the lipid-based shell.

Exteriorly-Positioned: This phrase indicates that the therapeutically active agent of a functionalized microbubble is located outside the lipid-based shell of the microbubble such that it extends from the exterior circumferential region and away from the core.

Halo (or halide or halogen): Fluoro, chloro, bromo, or iodo.

Haloaliphatic: An aliphatic group wherein one or more hydrogen atoms, such as one to 10 hydrogen atoms, independently is replaced with a halogen atom, such as fluoro, bromo, chloro, or iodo.

Haloaliphatic-aryl: An aryl group that is or can be coupled to a compound disclosed herein, wherein the aryl group is or becomes coupled through a haloaliphatic group.

Haloaliphatic-heteroaryl: A heteroaryl group that is or can be coupled to a compound disclosed herein, wherein the heteroaryl group is or becomes coupled through a haloaliphatic group.

Haloalkyl: An alkyl group wherein one or more hydrogen atoms, such as one to 10 hydrogen atoms, independently is replaced with a halogen atom, such as fluoro, bromo, chloro, or iodo. In an independent embodiment, haloalkyl can be a $CX_3$ group, wherein each X independently can be selected from fluoro, bromo, chloro, or iodo.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, silicon, boron, selenium, phosphorous, and oxidized forms thereof within the group. Alkoxy, ether, amino, disulfide, peroxy, and thioether groups are exemplary (but non-limiting) examples of heteroaliphatic.

Heteroaliphatic-aryl: An aryl group that is or can be coupled to a compound disclosed herein, wherein the aryl group is or becomes coupled through a heteroaliphatic group.

Heteroaryl: An aryl group comprising at least one heteroatom to six heteroatoms, such as one to four heteroatoms, which can be selected from, but not limited to oxygen, nitrogen, sulfur, silicon, boron, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group. Heteroaryl groups may be substituted with one or more groups other than hydrogen, such as aliphatic, heteroaliphatic, haloaliphatic, haloheteroaliphatic, aromatic, or an organic functional group.

Heteroatom: An atom other than carbon or hydrogen, such as (but not limited to) oxygen, nitrogen, sulfur, silicon, boron, selenium, or phosphorous. In particular disclosed embodiments, such as when valency constraints do not permit, a heteroatom does not include a halogen atom.

Interior Circumferential Region: A region of a lipid-based shell of a microbubble embodiment that defines a core of the microbubble.

Ketone: —C(O)$R^a$, wherein $R^a$ is selected from aliphatic, heteroaliphatic, haloaliphatic, haloheteroaliphatic, aromatic, or an organic functional group.

Lipid-Based Shell: A component of a microbubble that includes a single layer of lipids arranged in a spherical or substantially spherical arrangement. The lipids of the lipid-based shell can be a plurality of lipids that are identical species or they can be a plurality of lipids that are different species. The lipid-based shell has an interior circumferential region that defines the core of the microbubble and also has an exterior circumferential region that defines the outer perimeter of the microbubble.

Microbubble: A structure comprising lipid-based shell, wherein the shell defines a core comprising at least one gaseous reagent contained therein. In some embodiments, the lipid-based shell is further modified to comprise a therapeutically active agent attached thereto. In independent embodiments, microbubbles are structurally distinct from liposomes (e.g., echogenic liposomes). In such embodiments, the lipid-based shell of the microbubbles consists of, or consists essentially of, a single layer of lipids, whereas liposomes have a lipid bilayer and thus comprise at least two layers of lipids. In these embodiments, the lipid-based shell can be functionalized with a therapeutically active agent, a visualization agent, a targeting agent, additional therapeutically active agents, or any combinations thereof.

Organic Functional Group: A functional group that may be provided by any combination of aliphatic, heteroaliphatic, aromatic, haloaliphatic, and/or haloheteroaliphatic groups, or that may be selected from, but not limited to, aldehyde; aroxy; acyl halide; halogen; nitro; cyano; azide; carboxyl (or carboxylate); amide; ketone; carbonate; imine; azo; carbamate; hydroxyl; thiol; sulfonyl (or sulfonate); oxime; ester; thiocyanate; thioketone; thiocarboxylic acid; thioester; dithiocarboxylic acid or ester; phosphonate; phosphate; silyl ether; sulfinyl; thial; or combinations thereof.

Oxime: —C$R^a$=NOH, wherein $R^a$ is hydrogen, aliphatic, heteroaliphatic, haloaliphatic, haloheteroaliphatic, aromatic, or an organic functional group.

Peroxy: —O—O$R^a$ wherein $R^a$ is hydrogen, aliphatic, heteroaliphatic, haloaliphatic, haloheteroaliphatic, aromatic, or an organic functional group.

Pharmaceutically Acceptable Excipient: A substance, other than a compound that is included in a formulation of the compound. As used herein, an excipient may be incorporated within particles of a pharmaceutical composition, or it may be physically mixed with particles of a pharmaceutical composition. An excipient also can be in the form of a solution, suspension, emulsion, or the like. An excipient can be used, for example, to dilute an active agent and/or to modify properties of a pharmaceutical composition. Excipients can include, but are not limited to, antiadherents, binders, coatings, enteric coatings, disintegrants, flavorings, sweeteners, colorants, lubricants, glidants, sorbents, preservatives, adjuvants, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropyl cellulose, hydroxypropyl methylcellulose, xylitol, sorbitol, maltitol, gelatin, polyvinylpyrrolidone (PVP), polyethylene glycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin. In independent embodiments, water is not intended as a pharmaceutically acceptable excipient.

Phosphate: —O—P(O)(O$R^a$)$_2$, wherein each $R^a$ independently is hydrogen, aliphatic, heteroaliphatic, haloaliphatic, haloheteroaliphatic, aromatic, or an organic functional group; or wherein one or more $R^a$ groups are not present and the phosphate group therefore has at least one negative charge, which can be balanced by a counterion, $M^+$, wherein each $M^+$ independently can be an alkali ion, such as $K^+$, $Na^+$, $Li^+$; an ammonium ion, such as $^+N(R^b)_4$ where $R^b$ is H, aliphatic, heteroaliphatic, haloaliphatic, haloheteroaliphatic, or aromatic; or an alkaline earth ion, such as $[Ca^{2+}]_{0.5}$, $[Mg^{2+}]_{0.5}$, or $[Ba^{2+}]_{0.5}$.

Phosphonate: —P(O)(O$R^a$)$_2$, wherein each $R^a$ independently is hydrogen, aliphatic, heteroaliphatic, haloaliphatic, haloheteroaliphatic, aromatic, or an organic functional group; or wherein one or more $R^a$ groups are not present and the phosphate group therefore has at least one negative charge, which can be balanced by a counterion, $M^+$, wherein each $M^+$ independently can be an alkali ion, such as $K^+$, $Na^+$, $Li^+$; an ammonium ion, such as $^+N(R^b)_4$ where $R^b$ is H, aliphatic, heteroaliphatic, haloaliphatic, haloheteroaliphatic, or aromatic; or an alkaline earth ion, such as $[Ca^{2+}]_{0.5}$, $[Mg^{2+}]_{0.5}$, or $[Ba^{2+}]_{0.5}$.

Silyl Ether: $-OSiR^aR^b$, wherein each of $R^a$ and $R^b$ independently is selected from hydrogen, aliphatic, heteroaliphatic, haloaliphatic, haloheteroaliphatic, aromatic, or an organic functional group.

Subject: Living multi-cellular organisms, including vertebrate organisms, a category that includes both human and non-human mammals.

Sulfinyl: $-S(O)R^a$, wherein $R^a$ is selected from hydrogen, aliphatic, heteroaliphatic, haloaliphatic, haloheteroaliphatic, aromatic, or an organic functional group. In particular disclosed embodiments, the sulfinyl group can be sulfinic acid, having a structure $-S(O)R^a$, wherein $R^a$ is a OH group; or a sulfinate, having a structure $-S(O)R^a$, wherein $R^a$ is a OH group that has been deprotonated and the negative charge of the deprotonated oxygen atom may be balanced with an $M^+$ counter ion, wherein $M^+$ may be an alkali ion, such as $K^+$, $Na^+$, $Li^+$; an ammonium ion, such as $+N(R^b)_4$ where $R^b$ is H, aliphatic, heteroaliphatic, haloaliphatic, haloheteroaliphatic, or aromatic; or an alkaline earth ion, such as $[Ca^{2+}]_{0.5}$, $[Mg^{2+}]_{0.5}$, or $[Ba^{2+}]_{0.5}$. In yet some additional embodiments, the sulfinyl group can be sulfenic acid ($-S(O)H$) or the conjugate base thereof.

Sulfonyl: $-SO_2R^a$, wherein $R^a$ is selected from hydrogen, aliphatic, heteroaliphatic, haloaliphatic, haloheteroaliphatic, aromatic, or an organic functional group. In particular disclosed embodiments, the sulfonyl group can be sulfonic acid, having a structure $-S(O)_2R^a$, wherein $R^a$ is a OH group; or a sulfonate, having a structure $-S(O)_2R^a$, wherein $R^a$ is a OH group that has been deprotonated and the negative charge of the deprotonated oxygen atom may be balanced with an $M^+$ counter ion, wherein $M^+$ may be an alkali ion, such as $K^+$, $Na^+$, $Li^+$; an ammonium ion, such as $+N(R^b)_4$ where $R^b$ is H, aliphatic, heteroaliphatic, haloaliphatic, haloheteroaliphatic, or aromatic; or an alkaline earth ion, such as $[Ca^{2+}]_{0.5}$, $[Mg^{2+}]_{0.5}$, or $[Ba^{2+}]_{0.5}$.

Sulfonamide: $-SO_2NR^aR^b$ or $-N(R^a)SO_2R^b$, wherein each of $R^a$ and $R^b$ independently is selected from hydrogen, aliphatic, heteroaliphatic, haloaliphatic, haloheteroaliphatic, aromatic, or an organic functional group.

Sulfonate: $-SO_3^-$, wherein the negative charge of the sulfonate group may be balanced with an $M^+$ counter ion, wherein $M^+$ may be an alkali ion, such as $K^+$, $Na^+$, $Li^+$; an ammonium ion, such as $+N(R^b)_4$ where $R^b$ is H, aliphatic, heteroaliphatic, haloaliphatic, haloheteroaliphatic, or aromatic; or an alkaline earth ion, such as $[Ca^{2+}]_{0.5}$, $[Mg^{2+}]_{0.5}$, or $[Ba^{2+}]_{0.5}$.

Therapeutically effective amount: A quantity of compound or composition, for instance, a functionalized microbubble or a composition thereof, sufficient to achieve a desired effect in a subject being treated. For instance, this can be the amount sufficient to reduce the size of a thrombus or other vascular obstruction so as to provide sufficient blood flow through a vascular structure. Exemplary therapeutically effective amounts are disclosed herein; however, it will be understood that the effective amount administered will be determined by the physician in the light of the relevant circumstances including the condition to be treated, the choice of compound to be administered, and the chosen route of administration, and therefore dosage ranges of the present disclosure are not intended to be limiting. A therapeutically effective amount of compound is typically an amount such that when it is administered in a physiologically tolerable excipient composition, it is sufficient to achieve an effective systemic concentration or local concentration in the tissue.

Thial: $-C(S)H$.

Thiocarboxylic acid: $-C(O)SH$, or $-C(S)OH$.

Thiocyanate: $-S-CN$ or $-N=C=S$.

Thioester or Thionoester: $-C(O)SR^a$ or $-C(S)OR^a$ wherein $R^a$ is selected from hydrogen, aliphatic, heteroaliphatic, haloaliphatic, haloheteroaliphatic, aromatic, or an organic functional group.

Thioether: $-S$-aliphatic or $-S$-aromatic, such as $-S$-alkyl, $-S$-alkenyl, $-S$-alkynyl, $-S$-aryl, or $-S$-heteroaryl; or -aliphatic-S-aliphatic, -aliphatic-S-aromatic, -aromatic-S-aliphatic, or -aromatic-S-aromatic.

Thioketone: $-C(S)R^a$ wherein $R^a$ is selected from hydrogen, aliphatic, heteroaliphatic, haloaliphatic, haloheteroaliphatic, aromatic, or an organic functional group.

Treating/Treatment: Treatment of a disease or condition of interest in a subject, particularly a human or other animals having the disease or condition of interest, and includes by way of example, and without limitation:
(i) prophylactic administration to prevent the disease or condition from occurring in a subject, or to ameliorate symptoms associated with the condition if required in particular, when such subject is predisposed to the condition but has not yet been diagnosed as having it;
(ii) inhibiting the disease or condition, for example, arresting or slowing its development;
(iii) relieving the disease or condition, for example, causing regression of the disease or condition or a symptom thereof; or
(iv) stabilizing the disease or condition.

As used herein, the terms "disease" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

Introduction

Treatment for acute myocardial infarction (AMI) centers on timely percutaneous coronary intervention (PCI) for epicardial recanalization. Embolization of atherothrombotic debris during PCI for AMI is the key contributor to microvascular obstruction (MVO), which is common. MVO leads to microvascular hypoperfusion and worse clinical outcomes. There is no consistently efficacious therapy.

While microbubbles comprising tPA have been described by those in the art, such microbubbles do not provide the tPA molecules on the outside of the microbubble and instead embed them within the lipid shell of the microbubble. As such, delivery of tPA to the target of interest is limited. Also, liposomes comprising tPA have been developed in the art; however, these liposomes have reduced cavitational capacity compared to MBs, which limits the mechanical effectiveness for microvascular reperfusion.

New microbubble embodiments modified with one or more exteriorly-positioned therapeutically active agents are disclosed herein. In particular disclosed embodiments, the therapeutically active agent is a thrombolytic agent (e.g., tPA or a similar therapeutically active agent useful for promoting thrombolysis). These microbubble embodiments allow site specific delivery of the therapeutically active agent, such as a thrombolytic agent, directly to a vascular structure (e.g., an obstructed microvascular bed) and promote synergy between the therapeutically active agent and the cavitating microbubbles for thrombolysis and restoration of perfusion. In some embodiments, the microbubble embodiments also reduce dosages of thrombolytic agents as compared to amounts typically administered at systemic dosages and are able to localize delivery and avoid systemic administration of the thrombolytic agent. This is of particular interest for scenarios where systemic administration of thrombolytic agents is not feasible, such as when microvascular obstructions result from percutaneous coronary intervention for acute myocardial infarction. In yet additional embodiments, the functionalized microbubbles can reduce dosages of ultrasound energy used to activate the microbubbles, thereby minimizing off-target effects.

Functionalized Microbubbles and Compositions

Disclosed herein are embodiments of functionalized microbubbles. The functionalized microbubbles comprise a microbubble that is modified with at least one therapeutically active agent. In particular disclosed embodiments, the therapeutically active agent is chemically coupled to the outer lipid-based shell of the microbubble, such as through one or more of a covalent, electrostatic, ionic, and/or specific binding interaction. In particular embodiments, the lipid-based shell comprises an interior circumferential region that defines the core of the microbubble and an exterior circumferential region, which is attached to the therapeutically active agent. A representative schematic illustration of these regions of the microbubble are illustrated in FIG. 1; the therapeutically active agent is not illustrated. As shown in FIG. 1, microbubble 100 comprises an exterior circumferential region 102 and interior circumferential region 104 that defines core 106. In an independent embodiment, the therapeutically active agent is not embedded within the lipid-based shell of the microbubble and is not contained within the core of the microbubble as defined by the interior circumferential region of the lipid-based shell without the microbubble further comprises at least one therapeutically active agent attached to the exterior circumferential region of the lipid-based shell of the microbubble. In another independent embodiment, all therapeutically active agents are coupled to the exterior circumferential region of the lipid-based shell. In some embodiments, the functionalized microbubble can further comprise one or more of an additional therapeutically active agent, a visualization agent, a targeting agent, and any combinations thereof, wherein these components are included either in the core, embedded within the lipid shell, exteriorly-positioned, or any combinations thereof.

The lipid-based shell can comprise a plurality of lipids, wherein each lipid of the plurality is the same or different. The lipids can be selected from phospholipids (e.g., a phosphocholine-containing lipid, a phosphoethanolamine-containing lipid, a combination thereof); fatty acids (e.g., a saturated or unsaturated fatty acid); or any combinations thereof. In some embodiments, any of the lipids of the lipid-based shell can be functionalized with an alkylene oxide group, such as a polyalkylene oxide group (e.g., polyethylene oxide, or the like), and/or a specific binding pair member. In particular disclosed embodiments, the lipid-based shell comprises a mixture of 1,2-distearoylsn-glycero-3-phosphocholine (DSPC), 1,2-distearoyl-sn-glycero-3-phosphoethanolamine-N-[methoxy(polyethylene glycol)-2000]-biotin (DSPEPEG2k), and polyoxyethelene(40) stearate (PEG40S). In particular disclosed embodiments, the lipid-based shell comprises these three lipids in a weight ratio of 2:1:1 (DSPC:DSPEPEG2k:PEG40S).

The lipid-based shell is formed to define a core of the microbubble, which can comprise a gaseous reagent. Exemplary gaseous reagents can include, but are not limited to, air, hydrogen, nitrogen, oxygen, carbon dioxide, inert gases (e.g., helium, argon, xenon, krypton, or combinations thereof); sulfur fluorides (e.g., sulfur hexafluoride, disulfur decafluoride, or combinations thereof); hydrocarbons (e.g., alkanes, such as methane, ethane, propane, butane, or combinations thereof; cycloalkanes, such as cyclopropane, cyclobutane, cyclopentane, or combinations thereof; alkenes, such as ethylene, propene, or combinations thereof; alkynes, such as acetylene, propyne, or combinations; or combinations of such hydrocarbons); ethers; esters; halogenated hydrocarbons (e.g., fluoro-containing hydrocarbons, such as bromochlorodifluoromethane, chlorodifluoromethane, dichlorodifluoromethane, bromotrifluoromethane, chlorotrifluoromethane, ch loropentafluoroethane, dichlorotetrafluoroethane, chlorotrifluoroethylene, fluoroethylene, ethyl fluoride, 1,1-difluoroethane; perfluorocarbons, such as perfluoroalkanes, including perfluoromethane, perfluoroethane, perfluoropropanes, perfluorobutanes, perfluoropentanes, perfluorohexanes, and perfluoroheptanes; perfluoroalkenes, including perfluoropropene, and perfluorobutenes; and/or perfluorocycloalkanes, including perfluorocyclobutane; or any combinations thereof) or any combinations of such gaseous reagents. In some embodiments, the microbubble core comprises perfluorobutane.

In some embodiments, the microbubble is attached to least one therapeutically active agent and optionally to one or more additional therapeutically active agents, targeting agents, and/or visualization agents. The therapeutically active agent can be a thrombolytic agent capable of reacting with a thrombus to promote disruption, degradation, and/or destruction of the thrombus (e.g., to reduce the size of the thrombus such that blood perfusion is restored). In particular embodiments, the thrombolytic agent is a fibrinolytic agent, such as tissue plasminogen activator ("tPA"), a recombinant tissue plasminogen activator (e.g., Alteplase, Reteplase, Tenecteplase, Desmoteplase, or the like), a streptokinase activator (e.g., Anistreplase), or any combinations thereof. In particular disclosed embodiments, the thrombolytic agent is tPA. Exemplary additional therapeutically active agents that can be coupled to the microbubble include, but are not limited to, anticancer agents, antiplatelet drugs (e.g., aspirin, an adenosine diphosphate receptor inhibitor, a phosphodiesterase inhibitor, a protease-activated receptor-1 antagonist, a glycoprotein IIB/IIIA inhibitor, an adenosine reuptake inhibitor, or a thromboxane inhibitor), a protein (e.g., an antibody), a gene, a vector, or combinations thereof. Exemplary targeting agents can include, but are not limited to, p-selectin and other compounds that can target areas within a vascular or microvascular structure, which can, in some embodiments, include a glycoprotein IIB/IIIA inhibitor and/or an antibody. Exemplary visualization agents can include, but are not limited to, contrast agents, dyes, fluorophores, quantum dots, or other visually detectable agents.

In some embodiments, the microbubble is attached to least one therapeutically active agent using specific binding pair chemistry, such as biotin/streptavidin (or avidin, or a deglycosylated version thereof) chemistry. In yet other embodiments, the microbubble is attached to at least one therapeutically active agent via one or more covalent bonds formed between covalent binding partners, such as an organic functional group of a lipid of the microbubble and an organic functional group of the therapeutically active agent. In some embodiments, a linker can be used as spacer positioned between (and bound to) the microbubble and the therapeutically active agent. Exemplary covalent binding partners that can be used include thiol groups which can covalently bind with sulfur-reactive groups (e.g., another thiol group, a disulfide group, a carbon-carbon double bond, or a carbon-halide bond, such as —C(R$_2$)I, —C(R$_2$)Br, —C(R$_2$)F, —C(R$_2$)Cl, wherein each R independently is hydrogen, aliphatic, heteroaliphatic, haloaliphatic, haloheteroaliphatic, aromatic, or a combination thereof) and/or amine groups that can covalently bind with amine-reactive groups (e.g., isothiocyanates, isocyanates, sulfonyl chlorides, aldehydes, acyl azides, anhydrides, carbonates, NHS esters, imidoesters, epoxides, fluorophenyl esters or benzene, carboxylic acids, carboxylic acids modified with a carbodiimide, and the like).

Exemplary covalent binding partners can include a maleimide group present on a microbubble (as one partner) and a thiol group present on a therapeutically active agent (as the other partner); and/or a carboxylic acid group present on a microbubble (as one partner) that can be coupled with a carbodiimide (e.g., 1-Ethyl-3-(3-dimethylaminopropyl)carbodiimide, or "EDC"; or dicyclohexylcarbodiimide or "DCC") and a primary amine group present on a therapeutically active agent (as the other partner). In yet additional embodiments, the microbubble can be coupled to a liposome that comprises a therapeutically active agent encapsulated therein. In such embodiments, the liposome can be attached to the microbubble using coupling techniques disclosed herein.

If a linker is included, it can be a linker comprising an aliphatic group, a heteroaliphatic group, an aromatic group, a haloaliphatic group, an organic functional group, or any combinations thereof. In some embodiments, the linker can be selected to provide a particular distance between the microbubble and the therapeutically active agent, such as by increasing or decreasing the length of the linker. In yet additional embodiments, the linker can be selected to impart a particular solubility to the functionalized microbubble, such as by selecting a substantially hydrophilic linker or a substantially hydrophobic linker, or even a combination thereof. In representative embodiments, the linker can be 4-ethyl-N-(4-pentanamidobutyl)cyclohexane-1-carboxamide or a polyethylene glycol (or "PEG") group (e.g., PEG4). Similar chemical attachments and linkers can be used to functionalize the microbubble with one or more of an additional therapeutically active agent, a visualization agent, a targeting agent, and any combinations thereof.

In particular disclosed embodiments, the therapeutically active agent is a thrombolytic agent, such as tPA, and the thrombolytic agent is covalently attached directly or indirectly (such as through a linker group) to a biotin molecule to provide a biotin-functionalized therapeutically active agent. In such embodiments, the microbubble comprises a lipid-based shell that also is functionalized with one or more biotin molecules. The lipid-based shell of the microbubble can be further modified to comprise one or more streptavidin molecules, and/or avidin molecules (or a deglycosylated version thereof) that specifically bind to the biotin molecules attached to the microbubble.

Figure 2:
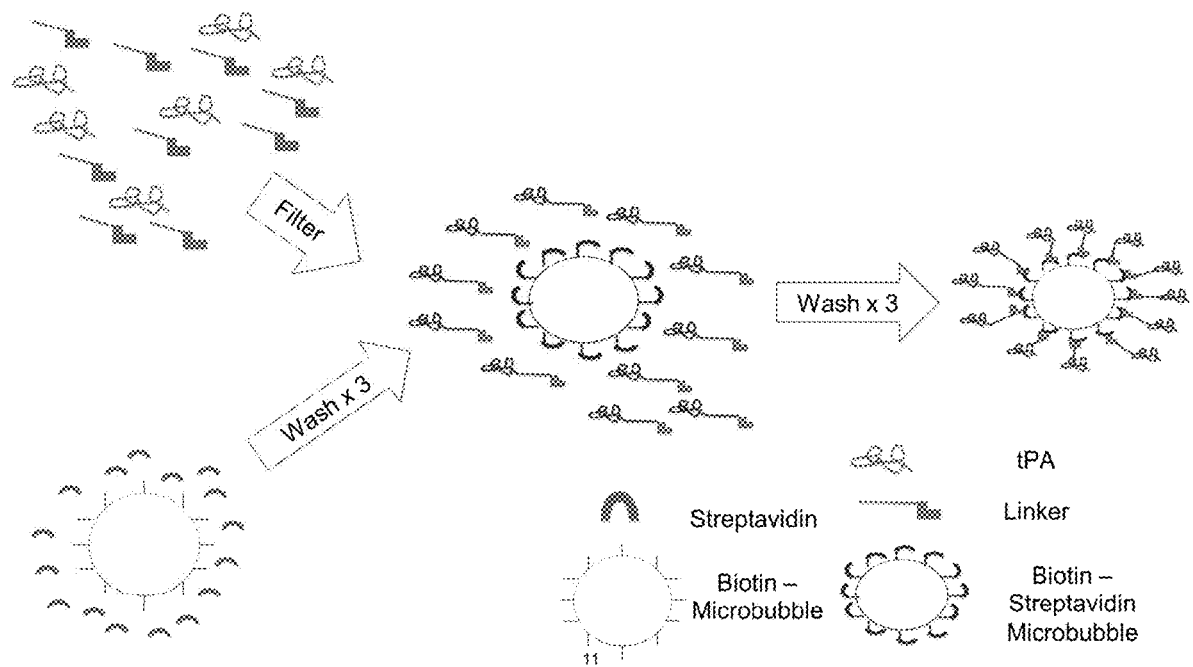
FIG. 2 is a schematic illustration of a representative process used to make a functionalized microbubble embodiment disclosed herein.

The biotin-functionalized thrombolytic agent is able to bind to the microbubble via biotin-streptavidin interactions (or biotin-avidin [or a deglycosylated version thereof] interactions) to provide the functionalized microbubble. A schematic illustrating a representative functionalized microbubble and a method of making the same is provided by FIG. 2. In particular disclosed embodiments, the biotin-functionalized thrombolytic agent comprises one or more thrombolytic agent molecules bound to a linker group, which in turn is bound to the biotin.

In yet other embodiments, the therapeutically active agent is a thrombolytic agent, such as tPA, and the thrombolytic agent is covalently attached directly or indirectly (such as through a linker) to one or more lipids of the microbubble via a thiol moiety of the thrombolytic agent. In such embodiments, the microbubble comprises one or more lipids that are attached directly or indirectly (such as through a linker) to one or more maleimide groups. The thiol group of the thrombolytic agent can covalently bind to the carbon-carbon double bond of the maleimide group, thereby forming a covalent linkage to the lipid-bases shell of the microbubble.

In yet other embodiments, the therapeutically active agent is a thrombolytic agent, such as tPA, and the thrombolytic agent is covalently attached directly or indirectly (such as through a linker) to one or more lipids of the microbubble via an amine moiety of the thrombolytic agent. In such embodiments, the microbubble comprises one or more lipids that have a carboxylic acid group (or that comprise one or more linkers having carboxylic acid groups). Using amide bond-forming reagents (e.g., EDC or DCC in combination with n-hydroxysuccinimide or "NHS"), the amine group of the thrombolytic agent can form an amide bond with the carboxylic acid group of the microbubble.

In some embodiments, at least one lipid of the lipid-based shell is coupled to the therapeutically active agent. In yet additional embodiments, a plurality of lipids can be coupled to a plurality of therapeutically active agents (which can be the same or different from one another), such that each lipid is coupled to one therapeutically active agent. In some embodiments, the concentration of the therapeutically active agent that is delivered to a subject or sample is controlled by controlling the lipid:therapeutically active agent ratio of the functionalized microbubble. In some embodiments, the functionalized microbubble can have a volumetric ratio of therapeutically active agent:microbubble ranging from 1:1 to 6:1, such as 1:1, 3:1, or 6:1. In some embodiments using a thrombolytic agent as the therapeutically active agent, the functionalized microbubble can be made with a lipid-to-thrombolytic agent ratio that provides a local tissue concentration ranging from greater than zero to 3 µg/mL of the thrombolytic agent upon administration to the subject or sample. In some embodiments, the lipid-to-thrombolytic agent ratio can be selected to provide a local tissue concentration ranging from 0.1 µg/mL to 2.5 µg/mL, or 0.1 µg/mL to 2 µg/mL, or 0.1 µg/mL to 1.5 µg/mL, or 0.1 µg/mL to 1 µg/mL, or 0.1 µg/mL to 0.5 µg/mL of the thrombolytic agent. In some embodiments, the functionalized microbubble comprises 1 e$^{-7}$ µg to 7 e$^{-7}$ µg of the thrombolytic agent (e.g., tPA) per microbubble, such as 1.2 e$^{-7}$ µg to 6.5 e$^{-7}$ µg of tPA per microbubble, or 1.5 e$^{-7}$ µg to 6 e$^{-7}$ µg of tPA per microbubble. In exemplary embodiments, the functionalized microbubble comprised 1.38 e$^{-7}$ µg of tPA per microbubble or 6.3 e$^{-7}$ µg of tPA per microbubble. In some embodiments, the amount of tPA loaded onto the functionalized microbubble is selected to provide a local tissue concentration (upon administration) that is 1% to 50% less than a typical systemic dose of tPA (which is generally recognized in the art to result in a plasma concentration of 3 µg/mL), such as 1% to 45%, or 1% to 40%, or 1% to 30%, or 1% to 20%, or 1% to 10% (e.g., 1%, 2%, 3%, 4%, 5%, 6%, 7%, 8%, 9%, or 10%) less than a systemic dose. Even at these lower dosages of tPA, the functionalized microbubble is able to promote thrombolysis of a thrombus as effectively, or even more effectively, as the systemic dose of tPA when used in method embodiments disclosed herein.

Also disclosed herein are composition embodiments comprising the functionalized microbubbles. Such composition embodiments can comprise one or more functionalized microbubble embodiments (which can be different, such as including different therapeutically active agents), and a pharmaceutically acceptable excipient, one or more additional therapeutically active agents, one or more visualization agents, one or more non-functionalized microbubbles, and any combinations thereof. The pharmaceutically acceptable excipient is "acceptable" in the sense of being compatible with the other ingredients of the formulation and not deleterious to the recipient thereof (a subject or sample). Proper formulation of the pharmaceutical composition is dependent upon the route of administration chosen. The composition embodiments disclosed herein may be manufactured in any manner known in the art with the benefit of the present disclosure, such as mixing, dissolving, granulating, dragee-making, levigating, emulsifying, encapsulating, entrapping, or compression processes. Exemplary additional therapeutics can include, but are not limited to, anticancer agents, aspirin, an adenosine diphosphate receptor inhibitor, a phosphodiesterase inhibitor, a protease-activated receptor-1 antagonist, a glycoprotein IIB/IIIA inhibitor, an adenosine reuptake inhibitor, or a thromboxane inhibitor. Exemplary visualization agents can include, but are not limited to, contrast agents, fluorophores, quantum dots, or other visually detectable agents.

Method of Making Functionalized Microbubbles

Disclosed herein are embodiments of a method for making the functionalized microbubble embodiments of the present disclosure. In some embodiments, the method comprises providing a specific binding pair member-functionalized microbubble and a specific binding pair member-functionalized therapeutically active agent and allowing them to interact such that the specific binding pair members bind together to conjugate the microbubble to the therapeutically active agent on the outside of the lipid-base shell of the microbubble. In particular disclosed embodiments, the specific binding pair member-functionalized microbubble comprises a streptavidin moiety and the specific binding pair member-functionalized therapeutically active agent comprises a biotin moiety and the two components are sufficiently mixed so that the biotin and the streptavidin moieties are able to specifically bind to provide the functionalized microbubble.

In yet additional embodiments, other conjugation methods, such as thiol-maleimide conjugation techniques, triazole formation techniques, and/or amide bond formation techniques can be used to covalently attach the therapeutically active agent to the microbubble. In some embodiments, a thiol moiety of a therapeutically active agent (e.g., a thrombolytic agent) is directly or indirectly (such as through a linker) coupled to a lipid of the microbubble that has been coupled to a maleimide group. In some such embodiments, tPA is used as the therapeutically active agent. tPA contains a total of 35 cysteines, and 34 of them are assigned to 17 disulfide bonds. Single cysteine-83 is therefore available for chemical modification. The bioconjugation of the tPA via Cysteine-83 does not significantly affect its thrombolytic activity. The maleimide-to-sulfhydryl conjugation between the thiol group terminating Cysteine-83 of the tPA and MB-maleimide particles produces a stable linkage. In some embodiments, given the small size of the tPA, a high loading of 1-100 µg of tPA per mg of NP/MB can be achieved. A representative scheme (Scheme 1) is provided below. As can be seen in Scheme 1, the sulfur atom of the thiol moiety covalently binds to a carbon atom of the carbon-carbon double bond of the maleimide group.

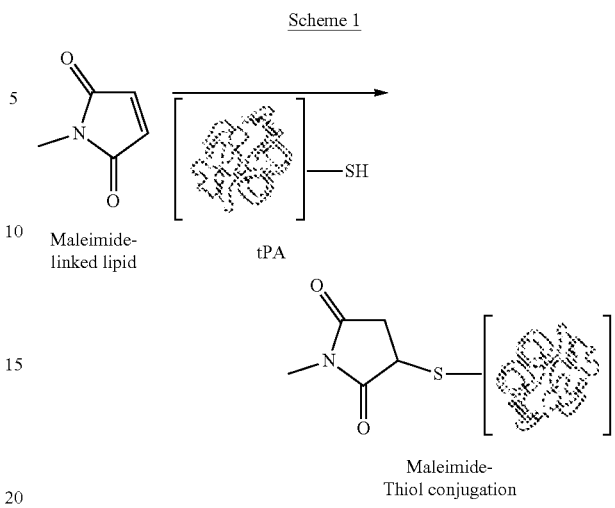

Scheme 1

Maleimide-Thiol conjugation

In yet some other embodiments, triazole click chemistry can be used to covalently couple the therapeutically active agent to the microbubble. In some such embodiments, one of the therapeutically active agent or the microbubble is functionalized with an azide moiety and the other is functionalized with an alkyne moiety. Copper(I)-based catalysis can then be used to promote triazole formation between the azide and the alkyne. And, in yet additional embodiments, an amine group of the therapeutically active agent can be coupled to a carboxylic acid group of a lipid using amide bond-forming reagents, such as EDC or DCC in combination with NHS. EDC coupling is used in some embodiments because it is water soluble, which allows direct bioconjugation without prior organic solvent dissolution. EDC reacts with carboxylic acid groups to form an active O-acylisourea intermediate that is easily displaced by nucleophilic attack from primary amino groups present on a therapeutically active agent. The primary amine forms an amide bond with the carbonyl carbon of a lipid on the lipid-based shell of the microbubble, and an EDC by-product is released as a soluble urea derivative. In some embodiments, N-hydroxysuccinimide (NHS) or N hydroxysulfoxuccinimide (sulfo-NHS) are used to improve efficiency or create dry-stable (amine-reactive) intermediates. The addition of Sulfo-NHS stabilizes the amine-reactive intermediate by converting it to an amine-reactive Sulfo-NHS ester, thus increasing the efficiency of EDC-mediated coupling reactions. In particular disclosed embodiments, covalent immobilization of a tPA molecule to one or more carboxylic acid groups of the lipids of the lipid-based shell of the microbubble using carbodiimide/succinimide chemistry (EDCNHS). The microbubble is incubated in a solution containing a 4:1-molar ratio of EDC and N-hydroxysuccinimide ester (NHS-ester) and stirred in the dark at 4° C. for 3 hours. Afterwards, the unreacted EDC/NHS are removed by ultrafiltration. Then, the activated carboxylic groups on the microbubbles are left to react with the tPA solutions prepared in 0.1 M phosphate buffer at 4° C. overnight. Thus, the activated carboxylic groups of microbubbles react with the terminal primary $NH_2$ groups of the tPA and form a stable covalent peptide bond.

In some embodiments, the method further comprises preparing a specific binding pair member-functionalized microbubble and a binding pair member-functionalized therapeutically active agent. The specific binding pair member-functionalized microbubble can be made by first mixing lipids together in a particular ratio (e.g., DSPC, DSPE-PEG2000-Biotin, and Peg40S in the ratio of 20 mg to 10 mg to 10 mg, respectively). The mixture is then dried and vortexed (e.g., dried under argon gas and vortex dried for 3 minutes). The mixture is then placed in a vacuum, and hydrolyzed with saline. The lipid solution is then placed into the sonicator until the solution becomes clear. At this point, the solution is placed under vacuum, at which point the gaseous reagent (e.g., PFC gas) is infused into the solution. The mixture is then placed in the sonicator for 75 seconds, at which point the microbubbles can be decanted from the solution.

Once the lipid-based shell comprising the specific binding pair member (e.g., biotin) is obtained, the microbubble can be reacted with the other member of the specific binding pair to provide the specific binding pair member-functionalized microbubble. In particular embodiments, the specific binding pair member-functionalized microbubble comprises a lipid-based shell functionalized with biotin that then binds with streptavidin (or avidin, or a deglycosylated version thereof) to provide a streptavidin-functionalized (or avidin-functionalized, or a deglycosylated avidin-functionalized) microbubble. The binding pair member-functionalized therapeutically active agent is made by combining the therapeutically active agent, such as a thrombolytic agent (e.g., tPA), with a specific binding pair member that is attached to a linker group for a time and under conditions sufficient to promote binding between a functional group of the therapeutically active agent (e.g., a thiol group or disulfide group of the thrombolytic agent) and a functional group present on the linker moiety (e.g., a sulfur-reactive group, such as a thiol group, a disulfide group, a carbon-carbon double bond, or a carbon-halide bond, such as —$CR_2I$, —$CR_2Br$, —$CR_2F$, —$CR_2Cl$, wherein each R independently is hydrogen, aliphatic, heteroaliphatic, haloaliphatic, haloheteroaliphatic, aromatic, or a combination thereof). In particular embodiments, the therapeutically active agent is tPA and a sulfur-containing functional group of the tPA molecule is reacted with a linker group comprising a carbon-carbon double bond, such as a maleimide group. In particular disclosed embodiments, the linker is a bifunctional linker, such as 4-ethyl-N-(4-pentanamidobutyl)cyclohexane-1-carboxamide or a polyethylene glycol (or "PEG") group (e.g., PEG4), and is bound to biotin at one end and a sulfur-reactive group on the other end that reacts with the tPA.

Method of Using Functionalized Microbubbles

Disclosed herein are embodiments of a method for using the functionalized microbubble embodiments of the present disclosure. The method can comprise using a functionalized microbubble (or a plurality thereof) to treat an obstruction in an artery, vein, or capillary, such as a microvascular obstruction, or a disease caused by or involving any such obstructions. In yet additional embodiments, the disclosed functionalized microbubbles can be used to promote, initiate, and/or enhance thrombolysis. In some embodiments, the method further comprises using ultrasound targeted microbubble cavitation (UTMC) to promote sonoreperfusion.

In particular disclosed embodiments, the method can comprise exposing a subject or a sample to a functionalized microbubble. Exposing can comprise administering the functionalized microbubble to a subject or a sample using a suitable administration method, such as injection or infusion routes. Suitable injection and/or infusion routes can include, but are not limited to, intravenous, intracerebroventricular, and/or intracranial routes. In particular disclosed embodiments directed to subjects, the functionalized microbubble is administered via intravenous injection. In some embodiments, the therapeutically active agent can direct delivery of the functionalized microbubbles to a targeted area, such as an area of the subject or sample that comprises a thrombus. In some embodiments, the therapeutically active agent is a thrombolytic agent (e.g., tPA), which can be used to direct the functionalized microbubble to a thrombus in view of the thrombolytic agent's ability to recognize/bind fibrin. In yet additional embodiments, the functionalized microbubble can be administered to a subject or sample in a location sufficient to deliver the functionalized microbubble to a thrombus via natural flow through a particular vascular structure. In additional embodiments, the functionalized microbubble can further comprise a targeting agent that facilitates targeted delivery of the microbubbles. In particular disclosed embodiments, the functionalized microbubbles are administered intravenously to a microvessel (e.g., an arteriole, a capillary, a metarteriole, a venule, or the like) of the subject that comprises a thrombus. In some embodiments, the functionalized microbubbles can be administered neat or as a composition, such as a composition embodiment as described herein.

Figure 3:
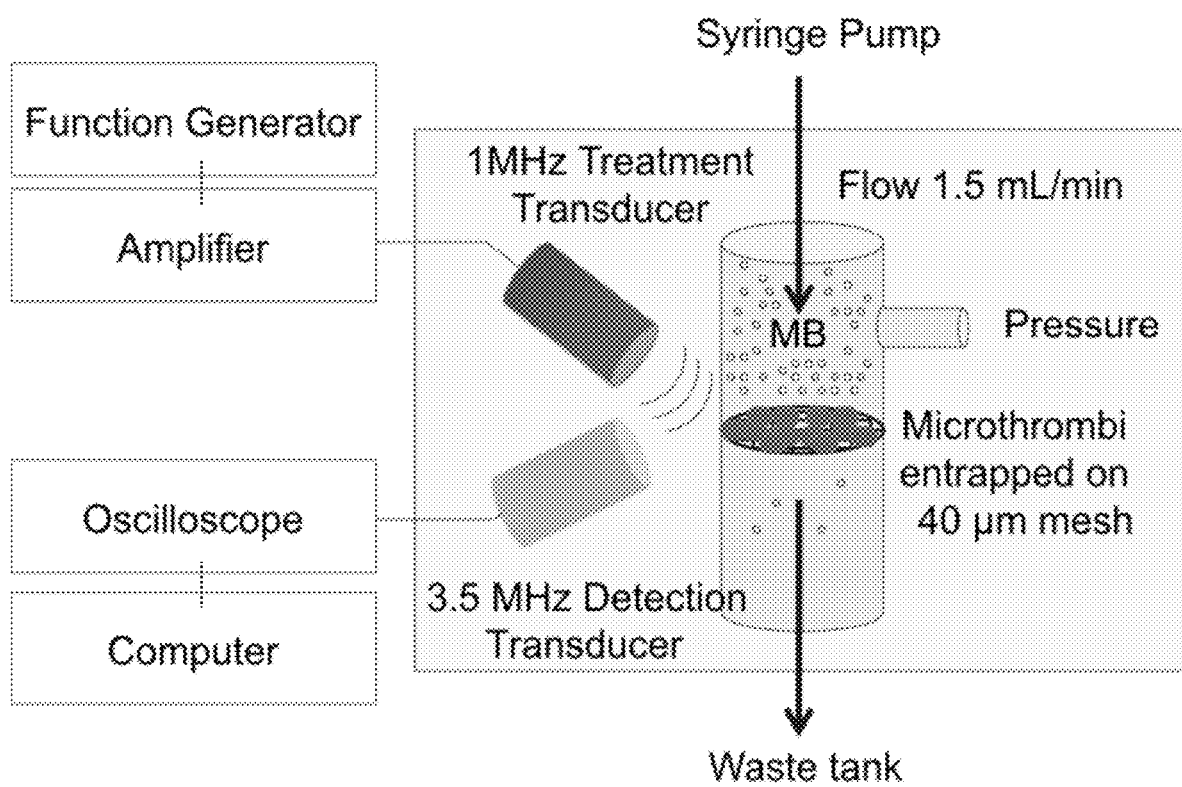
FIG. 3 is a schematic illustration of an in vitro flow model for evaluating microvascular obstruction.

In particular disclosed embodiments directed to samples (such as samples that are analyzed in vitro), the functionalized microbubble is administered to an in vitro flow system using syringe injection. An exemplary in vitro flow system is illustrated in FIG. 3. This system was used in examples described herein to establish the ability of the functionalized microbubbles to restore perfusion by disrupting a thrombus or other type of obstruction.

The method can further comprise using UTMC in combination with administering the functionalized microbubble by exposing the subject or sample to the functionalized microbubble and then applying one or more tone bursts of ultrasound within a vicinity of the functionalized microbubble. In such embodiments, UTMC can be used concurrently with administration of the functionalized microbubble or simultaneously (e.g., before or after administration of the functionalized microbubble). In embodiments using UTMC, tone bursts of ultrasound are delivered to an area of the subject or the sample where the functionalized microbubbles are located so as to promote inertial and stable cavitation of the functionalized microbubbles such that the thrombolytic agent can interact with any thrombus in the vicinity of the functionalized microbubbles. This cavitation can also promote visualization of the functionalized microbubbles. In some embodiments, the functionalized microbubbles are directed to a site within a microvessel that comprises a thrombus and initial cavitation of the functionalized microbubbles takes place. In particular disclosed embodiments, the therapeutically active agent can be cleaved from the microbubble. In yet additional embodiments, the therapeutically active agent does not need to be cleaved from the microbubble to be active. In such embodiments, bursting of the microbubble (e.g., disruption of the lipid-based shell) with sufficient ultrasound energy can allow the therapeutically active agent to react with the thrombus without ever being cleaved from the lipid-based shell. In some embodiments, the functionalized microbubbles form aggregates and continue to oscillate during ultrasound delivery. The prolonged acoustic activity can promote continued micro-streaming and mass transport of the therapeutically active agent. In addition, the prolonged acoustic activity can, at least in some embodiments, also promote continued sonoporation of cells and possible mass transport for materials like the additional therapeutically active agents disclosed herein (e.g., cancer drugs or gene vectors) in embodiments where the functionalized microbubbles might also be used to treat cells in combination with disrupting a thrombus.

In some embodiments, image guided therapy can be used to visualize the area of hypoperfusion to which the functionalized microbubbles are directed to determine whether a first administered dose is sufficient to promote thrombolysis. If it is determined that the size of the thrombus has not been sufficiently reduced (which can be evidenced by an inhomogenous distribution of microbubbles throughout the microcirculation area), a second dosage (or any number of subsequent dosages) of the functionalized microbubbles can be administered to deliver more of the thrombolytic agent to the thrombus. In some embodiments, the high speed imaging system disclosed by U.S. Patent Publication No. 2015/0141817, the relevant portion of which is incorporated herein by reference, can be used to visualize the functionalized microbubble after exposure by providing the ability to visualize microbubble acoustic behaviors, such as inertial cavitation. The ultrasound energy can be modified (e.g., increased or decreased) to facilitate disruption of the functionalized microbubbles.

In embodiments disclosed herein, the specific attributes of UTMC settings that are applied can vary based on the frequency desired for certain tissue types and organ size, the type of microbubble used, and the ultrasound pressure amplitude. For example, a tone burst of greater than 5 acoustic cycles can be used, such as a tone burst ranging from 10-5,000 acoustic cycles, or 1,000-2,000 acoustic cycles, with a pulse repetition frequency (PRF) that allows replenishment of the MB into the region of interest (ROI). In some embodiments, a PRF range of 0.01-20 Hz can be used, such as 0.2-1 Hz. An ultrasound frequency of 0.25 MHz-10 MHz can be used in some embodiments, such as 0.5 MHz to 5 MHz, or 0.75 MHz to 1.5 MHz. In some embodiments, a pressure amplitude of greater than 0.3 MPa can be used, such as a pressure amplitude of 0.5-2 MPa, or 0.75 to 1.5 MPa, or 0.75 to 1 MPa.

In some embodiments, UTMC can be applied at a "high" setting, which can comprise applying 1.5 MPa, at 1 MHz, PRF 0.33 Hz, for 5000 cycles, for a suitable period of time. In some other embodiments, UTMC can be applied at an "intermediate" setting, which can comprise applying 1.0 MPa, at 1 MHz, PRF 0.33 Hz, for 1000 cycles, for a suitable period of time. In yet additional embodiments, UTMC can be applied at a "low" setting, which can comprise applying 0.75 MPa, at 1 MHz, PRF 0.33 Hz, for 500 cycles, for a suitable period of time. In these "high," "intermediate," and "low" settings, the time period can range from five minutes (or less) to 30 minutes (or more) such as five minutes to 30 minutes, or 5 minutes to 20 minutes, or 5 minutes to 10 minutes.

Method embodiments disclosed herein can be used to deliver significantly lower amounts of a therapeutically active agent than are typically required without using the disclosed functionalized microbubbles and/or UTMC method embodiments. As such, the disclosed method embodiments can be used to treat a subject or sample while also avoiding any deleterious side effects that may result from using higher systemic amounts of the therapeutically active agent. The functionalized microbubbles also can facilitate decreasing the amount of ultrasound energy needed to achieve activation of microbubble cavitation, which can be beneficial to subjects that may have health issues necessitating lower ultrasound energies. In particular disclosed embodiments, the method embodiments are able to provide a high local therapeutic concentration, and low systemic load, of a thrombolytic agent (e.g., tPA), which minimizes bleeding risk. Also, the disclosed functionalized microbubble embodiments and method embodiments exhibit good activity without affecting the activity of the therapeutically active agent qualitatively or quantitatively.

In some embodiments, the functionalized microbubble is used to treat or prevent strokes, peripheral vascular disease, ischemia (e.g., acute ischemia), aneurysms, pulmonary embolism, sickle cell crisis, or any other disease caused by or involving blood clots or other vascular obstructions within the cardiovascular system.

Overview of Several Embodiments

Disclosed herein are embodiments of a functionalized microbubble. In some embodiments, the microbubble comprises: a microbubble comprising a lipid-based shell, wherein the lipid-based shell comprises (i) an interior circumferential region that defines a core of the microbubble and (ii) an exterior circumferential region; and at least one exteriorly-positioned thrombolytic agent attached to the exterior circumferential region of the lipid-based shell; wherein the at least one exteriorly-positioned thrombolytic agent extends from the exterior circumferential region and away from the core.

In some embodiments, the lipid-based shell comprises a single layer of a plurality of lipid species and wherein one or more of the lipid species of the plurality comprises a specific binding pair member; a linker group; a covalent binding partner group selected from a carboxylic acid group, a carbodiimide-modified carboxylic acid group, or a maleimide group; or any combination thereof.

In any or all of the above embodiments, the specific binding pair member is biotin, streptavidin, avidin, or a deglycosylated avidin.

In any or all of the above embodiments, the exteriorly-positioned thrombolytic agent comprises a covalent binding partner group selected from an amine or a thiol group; a specific binding pair member; a linker group; or a combination thereof. In some embodiments, the specific binding pair member is biotin. In yet some additional embodiments, each linker group independently comprises an aliphatic group, a heteroaliphatic group, an aromatic group, an organic functional group, or any combination thereof.

In any or all of the above embodiments, the exteriorly-positioned thrombolytic agent is a tissue plasminogen activator.

In any or all of the above embodiments, the exteriorly-positioned thrombolytic agent is directly or indirectly covalently attached to at least one lipid of the lipid-based shell or is directly or indirectly attached to at least one lipid of the lipid-based shell through interactions between members of a specific binding pair.

In any or all of the above embodiments, the exteriorly-positioned thrombolytic agent is encapsulated in a liposome and the liposome is attached to the exterior circumferential region of the lipid-based shell. In some embodiments, the liposome is directly or indirectly covalently attached to at least one lipid of the lipid-based shell or is directly or indirectly attached to at least one lipid of the lipid-based shell through interactions between members of a specific binding pair.

In any or all of the above embodiments, the functionalized microbubble can comprise an amount of the exteriorly-positioned thrombolytic agent ranging from 1 $e^{-7}$ μg to 7 $e^{-7}$ μg.

In any or all of the above embodiments, the functionalized microbubble can further comprise an additional therapeutically active agent, a visualization agent, a targeting agent, or any combination thereof. In some embodiments, the additional therapeutically active agent, the visualization agent, the targeting agent, or any combination thereof is attached to the exterior circumferential region of the lipid-based shell; or is embedded in the lipid-based shell; or is located in the core of the microbubble; or any combinations thereof. In yet some additional embodiments, the additional therapeutically active agent is an anticancer agent, a gene, a protein, or an antiplatelet drug; the visualization agent is a contrast agent, a fluorophore, a quantum dot, or a dye; and/or the targeting agent is p-selectin.

Also disclosed herein are embodiments of a therapeutic composition, comprising: a functionalized microbubble; and a pharmaceutically acceptable excipient, one or more additional therapeutically active agents or visualization agents, or any combinations thereof. In some embodiments, the therapeutic composition further comprises a microbubble that is not functionalized with a thrombolytic agent.

Also disclosed herein are embodiments of a method, comprising: exposing a subject or a sample to the functionalized microbubble of any one or more of the above embodiments, or the therapeutic composition of any one or more of the above therapeutic composition embodiments; and applying an ultrasound tone burst within a vicinity of the functionalized microbubble.

In some embodiments, the method comprises exposing a subject to the functionalized microbubble or the therapeutic composition by administering the functionalized microbubble or the therapeutic composition via intravenous injection. In some embodiments, the intravenous injection is into a microvessel comprising a thrombus or other microvascular obstruction.

In any or all of the above embodiments, the ultrasound tone burst is sufficiently energetic so as to cause disruption of the functionalized microbubble by disrupting the lipid-based shell, releasing the exteriorly-positioned thrombolytic agent from the lipid-based shell, or a combination thereof. In some embodiments, the ultrasound tone burst is an ultrasound tone burst of greater than 5 acoustic cycles with both (i) a pulse repetition frequency of between 0.01 and 20 Hz; and (ii) a pressure amplitude of greater than 0.3 MPa. In yet additional embodiments, the ultrasound tone burst is an ultrasound tone burst comprising 5000 cycles at 1 MHz, with both a pulse repetition frequency of 0.33 Hz and applying a pressure amplitude of 1.5 MPa; an ultrasound tone burst comprising 1000 cycles at 1 MHz, with both a pulse repetition frequency of 0.33 Hz and applying a pressure amplitude of 1.0 MPa; ultrasound tone burst comprising 500 cycles at 1 MHz, with both a pulse repetition frequency of 0.33 Hz and applying a pressure amplitude of 0.75 MPa; or any combination thereof.

In any or all of the above embodiments, the method can further comprise visually detecting the microbubble in the subject or the sample by detecting microbubble inertial cavitation after exposing applying the ultrasound tone burst.

In any or all of the above embodiments, the method is used to treat or prevent strokes, peripheral vascular disease, ischemia (e.g., acute ischemia), aneurysms, pulmonary embolism, sickle cell crisis, or any other disease caused by or involving blood clots or other vascular obstructions.

Also disclosed herein are embodiments of a method for treating a microvascular obstruction in a microvascular structure, comprising: exposing a subject or a sample to the functionalized microbubble of any one or more of the above embodiments, or the therapeutic composition of any one or more of the above therapeutic composition embodiments; visualizing the functionalized microbubble in the subject or the sample after exposure; applying one or more tone bursts of ultrasound within a vicinity of the functionalized microbubble once the functionalized microbubble is in proximity of a thrombus; and reducing a size of the thrombus to a size sufficient to remove the microvascular obstruction and allow blood flow to continue through the microvascular structure.

EXAMPLES

Example 1

In this example, tPA-functionalized microbubble embodiments were made by linking tPA to biotin, using either BMCC-biotin or NHS-PEG4-Biotin. In one example, tPA was dissolved in PBS at 1 mg/mL. An 8 mM BMCC stock solution was used, and 20 uL was added to 1 mL of tPA solution for reaction. The mixture was reacted at 4° C. overnight and then filtered utilizing Zeba Desalting Column. The biotinylated tPA (0.4 mg/mL) was then mixed and incubated with microbubbles comprising a streptavidin-labeled lipid-based shell via biotin-streptavidin specific pair binding (1×109/mL). Then, the product was washed twice with PBS to form tPA loaded MB (preparation ratio was $4 \times 10^{-13}$ g tPA/MB). The microbubbles comprised DSPC, DSPE-PEG 2000-Biotin, and PEG40S-polyoxyethylene(40) stearate. The microbubbles were made with the following procedure: Phospholipid encapsulated microbubbles were prepared from a lipid aqueous dispersion composed of polyoxyethylene (40) stearate (Sigma-Aldrich; St. Louis, MO), 1,2-distearoyl-sn-glycero-3-phosphocholine (DSPC) and 1,2-distearoyl-sn-glycero-3-phosphoethanolamine-N-[biotinyl(polyethylene glycol)-2000] (DSPE-PEG2000-biotin; Avanti polar lipids; Alabaster, AL). Briefly, polyoxyethylene (40) stearate, DSPC and DSPE-PEG2000-biotin (1:2:1, w/w/w) were dissolved in chloroform. The chloroform was evaporated by flushing with argon and followed by an overnight vacuum-dry. The dried lipid film was rehydrated in saline with a final lipid concentration of 10 mg/ml for 4 hours at room temperature. After a brief sonication to dissolve any lipid debris, the lipid dispersion was sonicated with a 20 kHz probe in the presence of perfluorobutane gas. After sonication, the microbubbles were washed with saline two to three times to remove any free lipid and suspended in saline saturated with perfluorobutane. For tPA loaded MB, DSPE was replaced by DSPE-mPEG 2000-Biotin, resulting in biotinylated MBs. The biotinylated MBs ($5 \times 10^8$ MB/mL) were incubated with Streptavidin (2.1 mg/mL) for 1 hour at 4° C. and washed with saline to remove excess free streptavidin. Similar conditions were used to make the NHS-PEG4-Biotin embodiments.

Example 2

In this example, the ability of the functionalized microbubbles disclosed herein to lyse a thrombus was evaluated in vitro. A thrombus was generated by allowing citrated porcine blood and 25 mM $CaCl_2$) to mix for two hours. A plurality of tPA-functionalized microbubbles (from a stock solution of 1 e9 microbubble/mL, wherein the microbubbles were modified with tPA in a volumetric ratio of 1:1 tPA:microbubble) were added to a PBS-buffered solution comprising the thrombus and then the samples were exposed to sonication to promote interaction between the tPA and the thrombus. The mass of the thrombus was then weighed after 4 and 20 hours. Results are shown in FIGS.

Figure 4A:
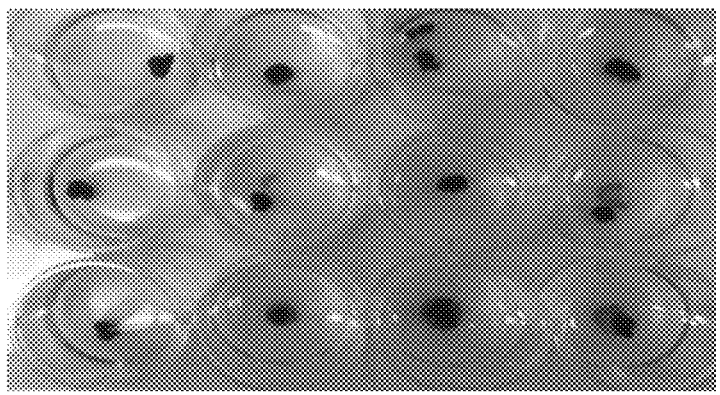
FIGS. 4A-4D are photographic images of various samples that were prepared and evaluated to determine the ability of functionalized microbubble embodiments to reduce thrombus size in combination with ultrasound treatments.
Figure 4B:
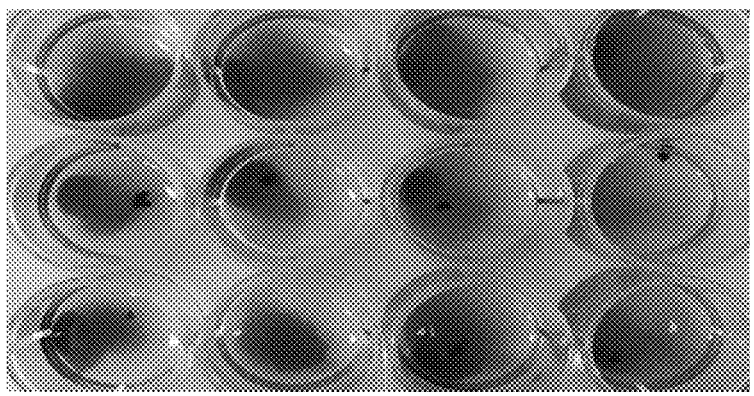
Figure 4C:
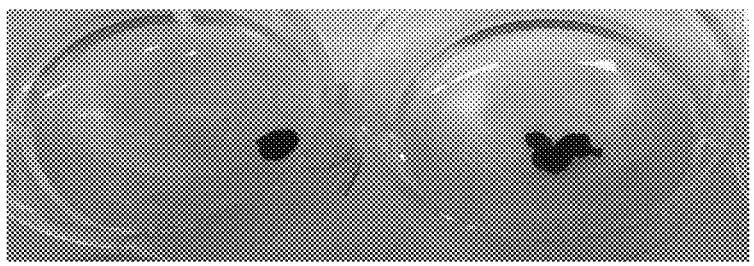
Figure 4D:
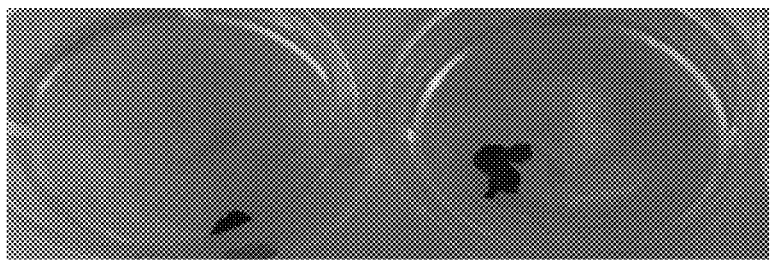
Figure 5:
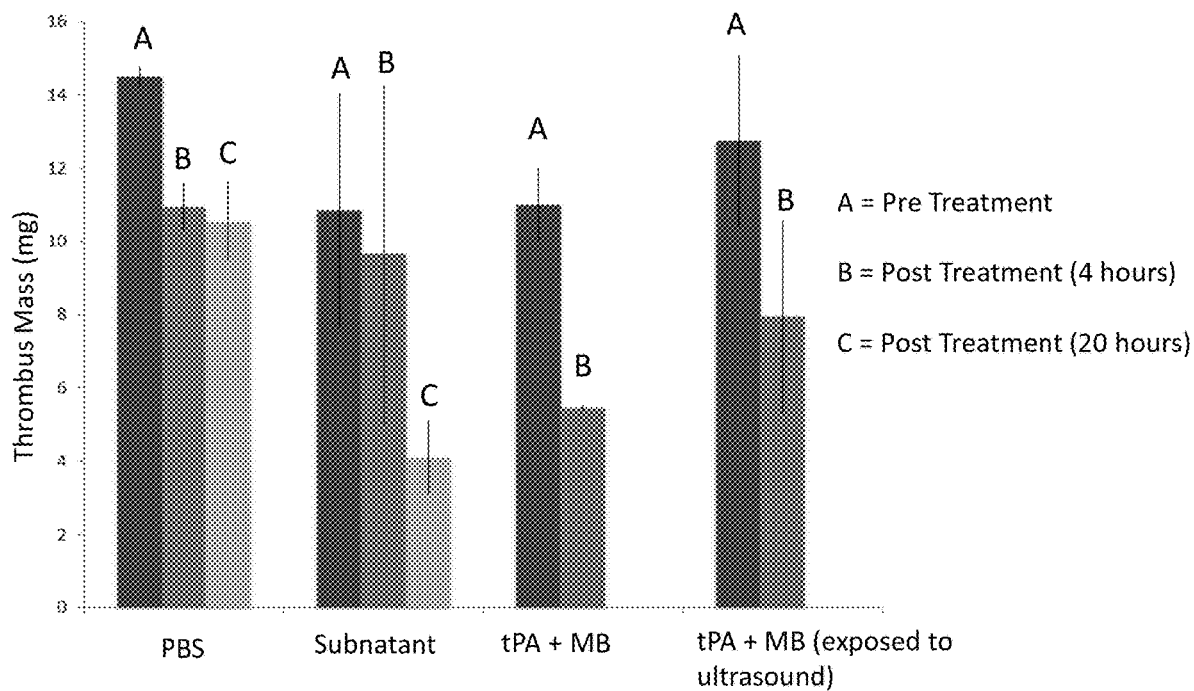
FIG. 5 is a graph of thrombus mass (mg) as a function of treatment protocol showing results obtained from assessing certain samples of FIGS. 4A-4D.

4A-4D. PBS buffer control samples were used (FIGS. 4C and 4D), along with samples exposed to tPA alone (top row in FIGS. 4A and 4B). Rows 2 and 3 of FIGS. 4A and 4B show the samples comprising the tPA-functionalized microbubbles and the samples comprising the tPA-functionalized microbubbles pre-burst, respectively. The "pre-burst" microbubbles refers to microbubbles incubated within the well and that were disrupted within an ultrasound beam. These were used as control samples to show that the tPA-functionalized microbubbles that were not "pre-burst" did not exhibit clot lysis until affirmatively burst with ultrasound. FIG. 5 provides quantitative in vitro proof of lysis of the porcine venous thrombus with tPA-functionalized microbubbles (or pre-burst tPA-functionalized microbubbles) as it shows complete lysis of the thrombus after 20 hours.

Example 3

Figure 6:
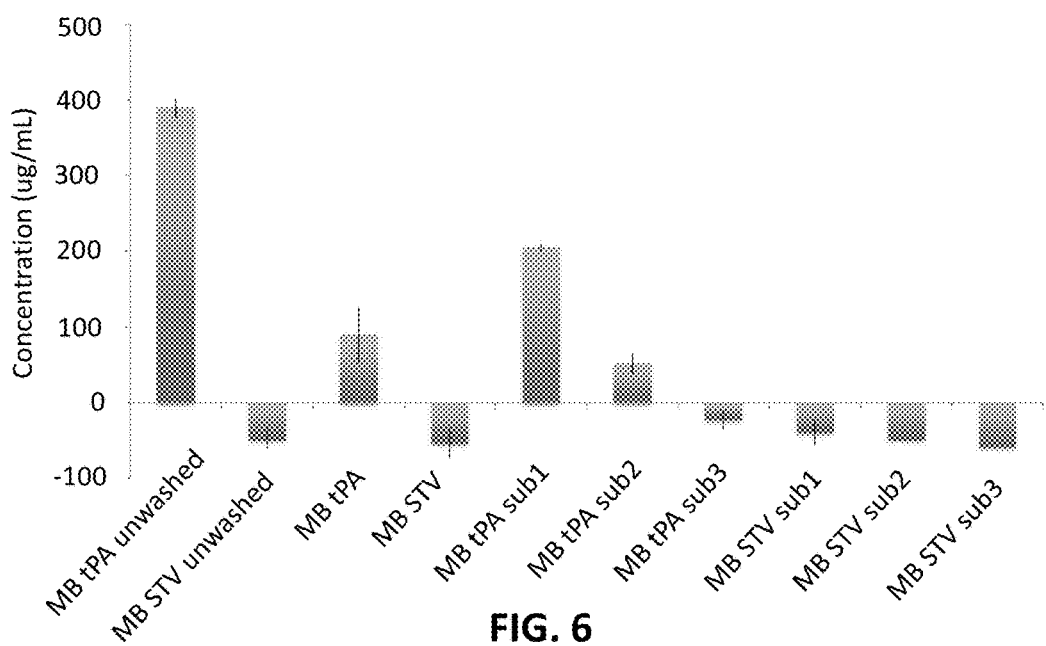
FIG. 6 is a graph showing results from evaluating tPA concentration in certain tPA-functionalized microbubble embodiments determined using a BCA protein assay.

In this example, a BCA assay was used to quantify the amount of tPA included per microbubble in certain functionalized microbubble embodiments. The BCA protein assay measures the total protein amounts in a sample. Two different tPA-functionalized microbubble embodiments were evaluated, one comprising tPA attached to a microbubble via a biotin moiety included with a BMOC linker and one comprising tPA attached to a microbubble via a biotin moiety included with an NHS linker (NHS-PEG4-Biotin). For the BMOC linker embodiments, 10% of the stock solution of tPA was loaded onto a microbubble and the resulting amount of tPA on the microbubble was determined to be $6.3 \pm 2.2 \text{ e}^{-7}$ μg of tPA per microbubble. Results for this embodiment are summarized in FIG. 6. For the NHS linker embodiments, 10-12% of the stock solution of tPA was loaded onto a microbubble and the resulting amount of tPA on the microbubble was determined to $1.38 \text{ e}^{-7}$ μg of tPA per microbubble. The microbubble plus streptavidin was measured with and without tPA using 2% SDS to mask any lipid effects. A 3:1 volumetric ratio of tPA to microbubble was used in some examples. tPA concentration was determined utilizing the BCA protein assay (with a minimum detectible range of 20 μg/mL). Washing three times successfully removed unloaded tPA. No protein signal measured in all testing samples when coupled to the microbubble.

Example 4

Figure 7:
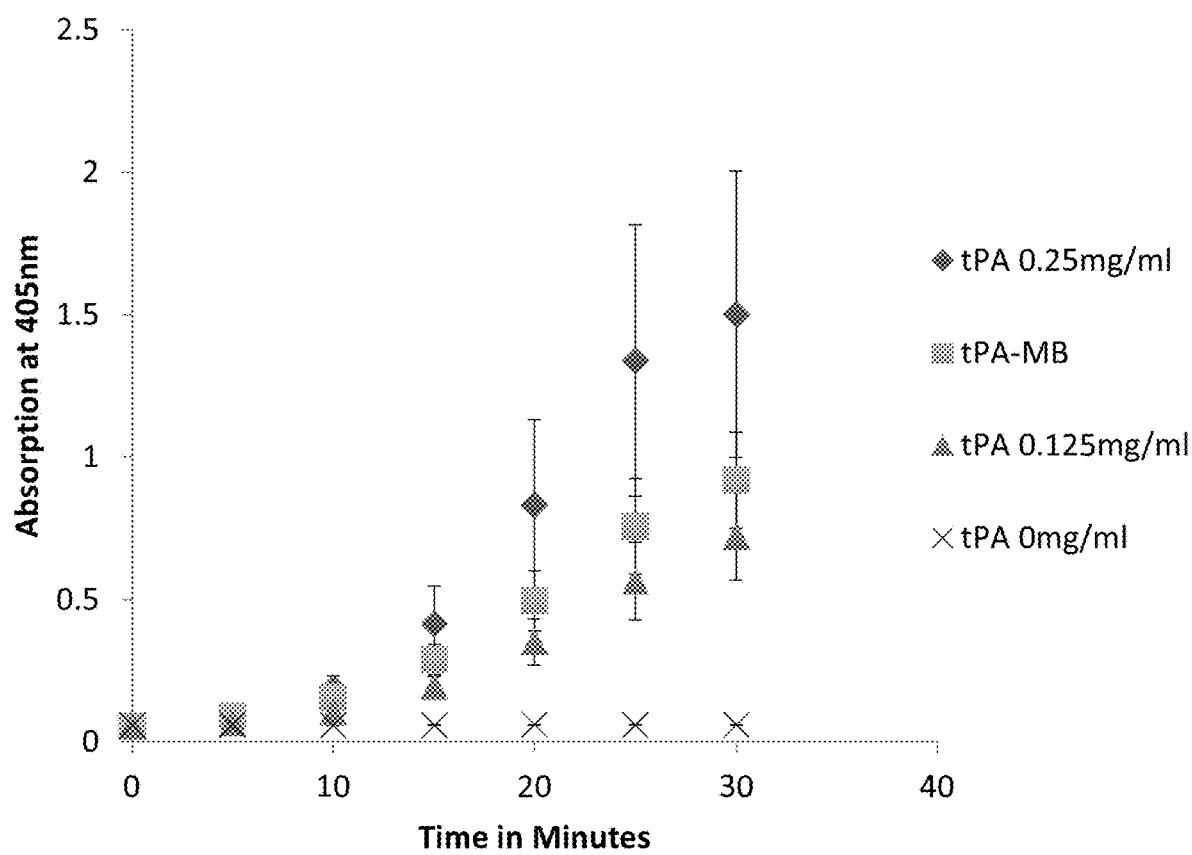
FIG. 7 is a graph of absorption at 405 nm as a function of time (minutes) that confirms that the activity of tPA is not deleteriously affected by attaching tPA to a microbubble embodiment.

In this example, a tPA activity assay was used to measure the ability of tPA, provided by a functionalized microbubble embodiment, to convert plasminogen to plasmin. A synthetic plasmin substrate was used, which comprised a cleavable chromophore. Upon cleavage, the absorption of the cleaved chromophore was measured to determine the activity of the tPA of the microbubble and the results compared to a tPA standard curve. FIG. 7 shows results obtained for the functionalized microbubble embodiment used in this example (namely, the NHS linker-containing embodiment discussed above in Example 3).

Example 5

Figure 8:
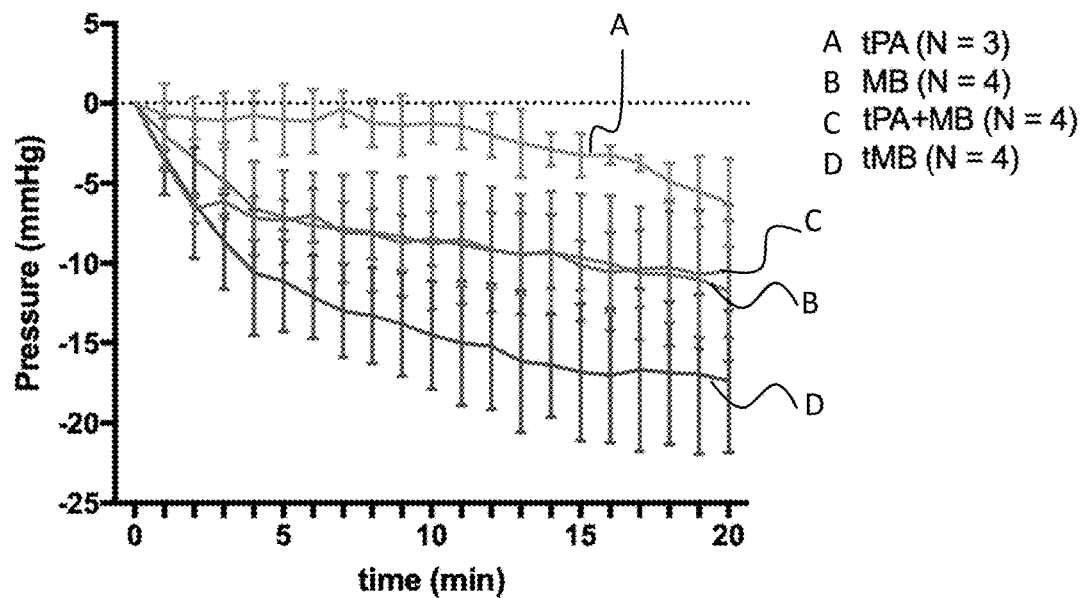
FIG. 8 is a graph of pressure (mmHg) as a function of time (minutes) showing results obtained from analyzing activity of various samples (full dose tPA alone ("A"); non-functionalized microbubbles in combination with ultrasound ("B"); full dose tPA in combination with non-functionalized microbubbles and ultrasound ("C"); and tPA-functionalized microbubbles in combination with ultrasound ("D") using an in vitro flow model system.
Figure 9:
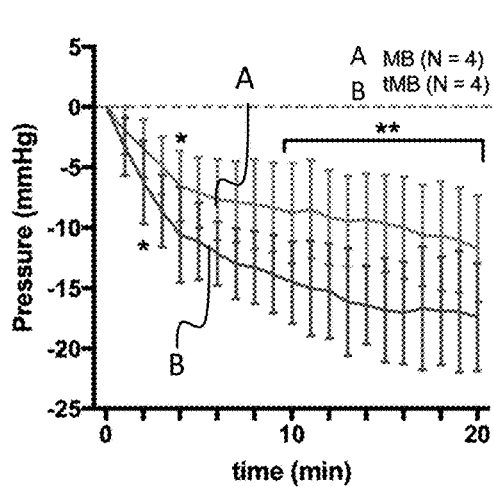
FIG. 9 is a graph of pressure (mmHg) as a function of time (minutes) showing a comparison of the results obtained from analyzing activity of non-functionalized microbubbles in combination with ultrasound ("A") and tPA-functionalized microbubbles in combination with ultrasound ("B") using an in vitro flow model system.
Figure 10:
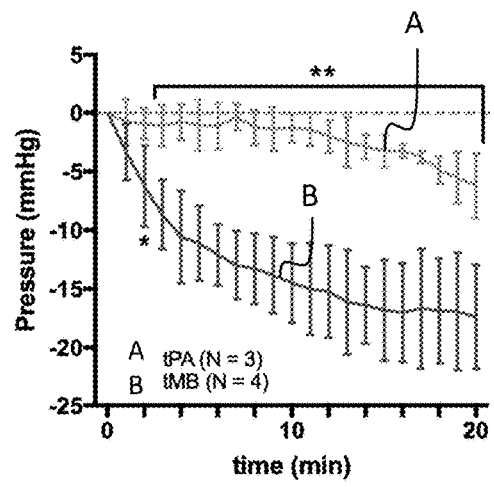
FIG. 10 is a graph of pressure (mmHg) as a function of time (minutes) showing a comparison of the results obtained from analyzing activity of full dose tPA alone ("A") and tPA-functionalized microbubbles in combination with ultrasound ("B") using an in vitro flow model system.
Figure 11:
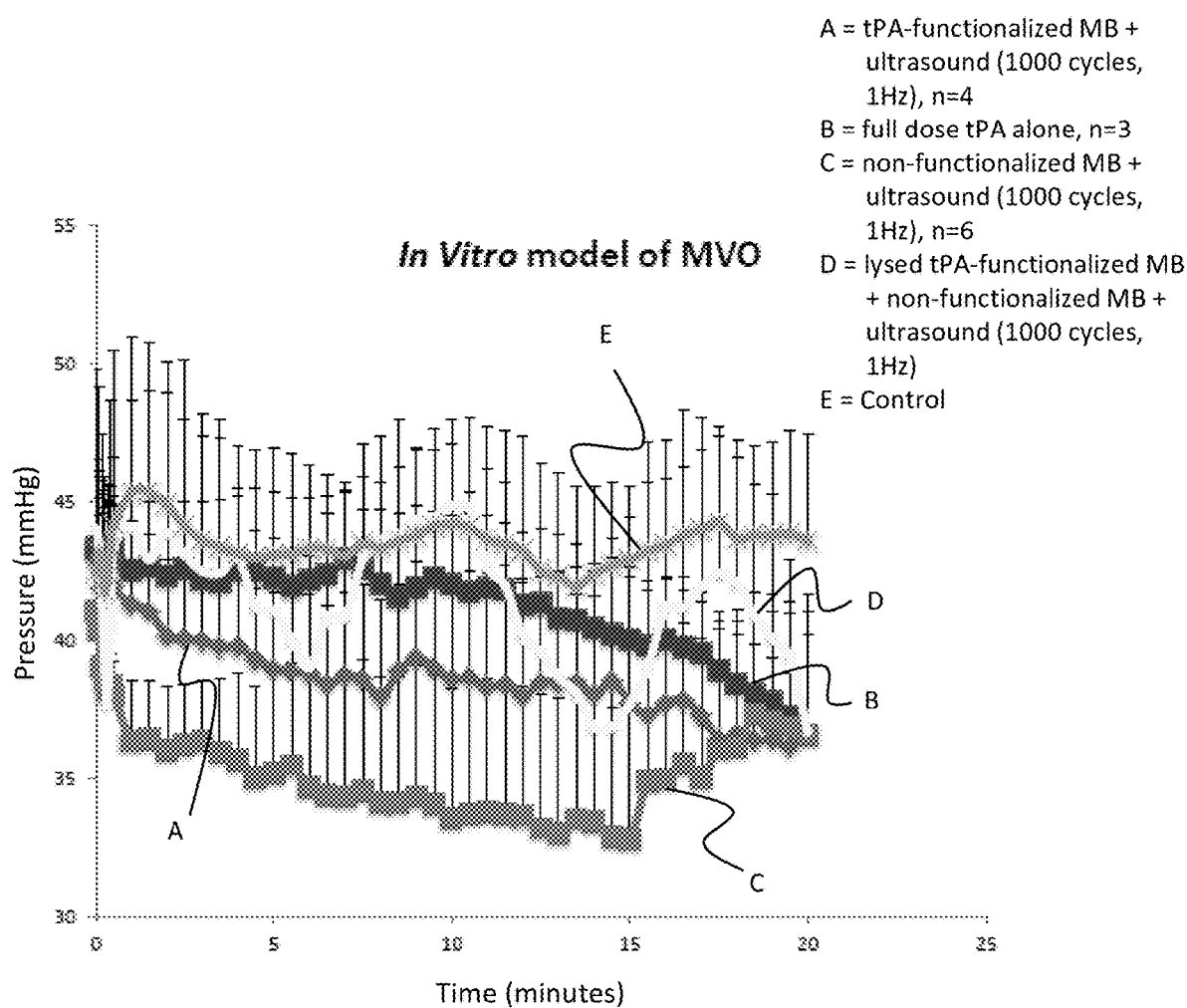
FIG. 11 is a graph of pressure (mmHg) as a function of time (minutes) showing results obtained from analyzing activity of various samples (tPA-functionalized microbubbles in combination with ultrasound ("A"), full dose tPA alone ("B"); non-functionalized microbubbles in combination with ultrasound ("C"); lysed tPA-functionalized microbubbles in combination with non-functionalized microbubbles, and ultrasound ("D"); and a control ("E")) using an in vitro flow model system.

In this example, an in vitro flow loop model was used to determine the ability of tPA-functionalized microbubble embodiments to promote sonoreperfusion. Four different samples were run using the flow loop model set-up illustrated in FIG. 3: (1) tPA-functionalized microbubbles in combination with ultrasound tone bursts (1 MHz, 1 MPa, 1000 cycles, every three seconds); (2) a non-functionalized microbubble in combination with ultrasound tone bursts (1 MHz, 1 MPa, 1000 cycles, every three seconds); a full dose of tPA at 3 μg/ml (or 90 μg) in combination with a non-functionalized microbubble, and ultrasound tone bursts (1 MHz, 1 MPa, 1000 cycles, every three seconds); and a full dose of tPA alone with no ultrasound or microbubbles. The functionalized and non-functionalized microbubbles were provided at a concentration of $6 \text{ e}^7$ microbubbles per run (30 μL). Results are shown in FIGS. 8-10. Additional results are shown in FIG. 11, which includes activity results for (i) tPA-functionalized microbubbles, (ii) full dose tPA alone, (iii) non-functionalized microbubbles in combination with ultrasound; (iv) pre-burst tPA-functionalized microbubbles in combination with non-functionalized microbubbles and ultrasound; and a control (PBS buffer as the perfusate). The starting pressure was 40 mmHg and results were normalized to show pressure decrease throughout each sample run. As can be seen by the results in FIGS. 8-11, there was a significant decrease in upstream pressure for the tPA-functionalized microbubble embodiments (with ultrasound) as compared to the other sample runs, indicating successful thrombus disruption. Upstream pressure was measured as an indication of thrombus burden and reperfusion. In particular embodiments, the tPA-functionalized microbubbles contained a maximum tPA concentration of 0.8 μg/mL (assuming 100% binding efficiency), which is ~¼ the amount of tPA in a systemic dose (which typically is 3 μg/mL).

Example 6

Figure 12:
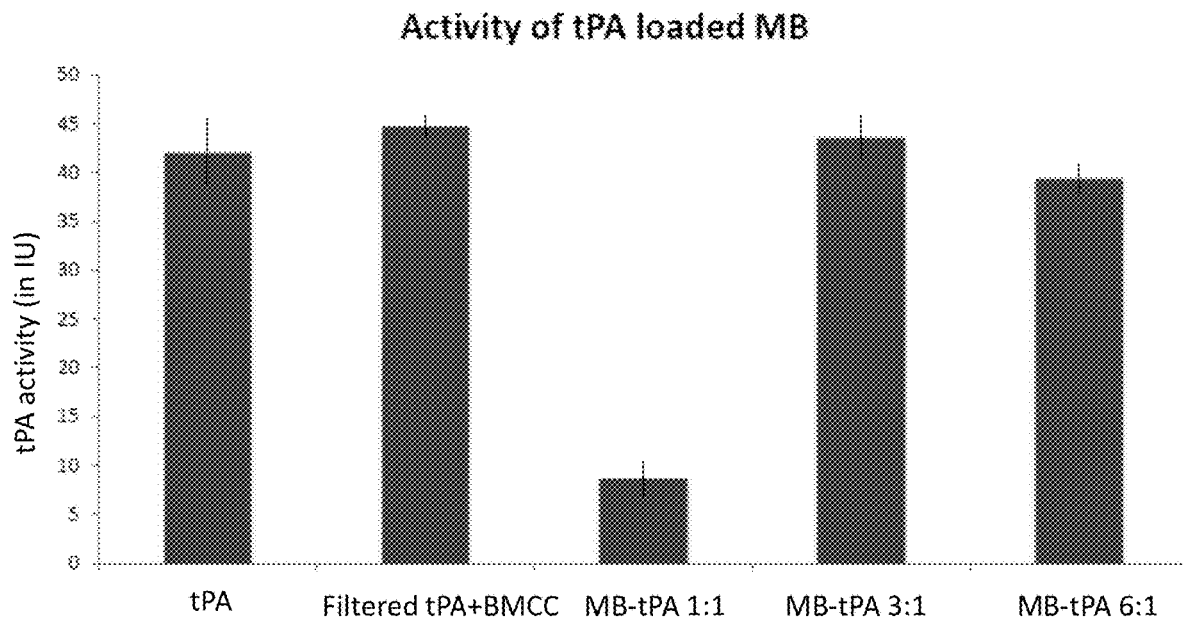
FIG. 12 is a bar graph showing results obtained from analyzing the activity of modified tPA, which confirms that functionalizing microbubbles with tPA does not decrease the enzymatic activity of the tPA.
Figure 13:
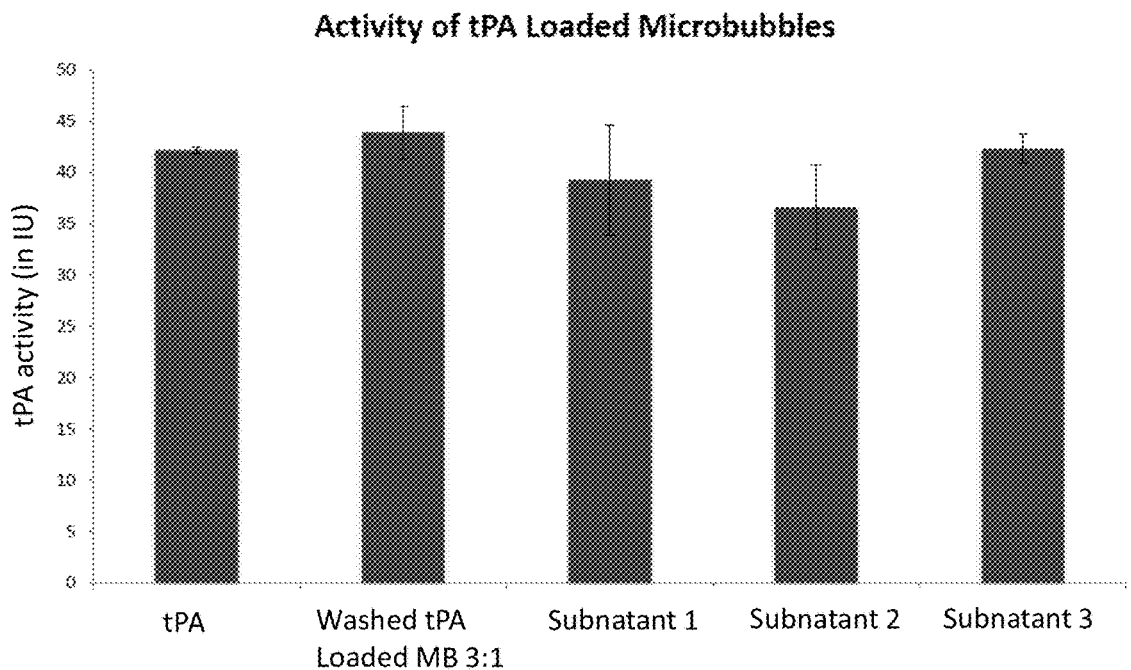
FIG. 13 is a bar graph showing results obtained from analyzing the activity of modified tPA, wherein tPA activity was detected in the wash subnatant following microbubble functionalization.

In this example, tPA-functionalized microbubble embodiments were evaluated to determine if attaching the tPA to the microbubble had any deleterious effect on the enzymatic activity of the tPA. The tPA-functionalized microbubble embodiments were prepared at a volumetric ratios of 3:1 and 6:1 (concentration of tPA to microbubble). Results are shown in FIGS. 12 and 13. These results confirm that functionalizing the microbubble with tPA did not decrease the enzymatic activity of the tPA. For FIG. 12, base tPA was 1 mg/mL and filtered tPA-BMCC was 0.87 mg/mL. The BCA protein assay was used in this example, which is a commercially available assay utilizing bicinchoninic acid to measure protein concentration. This is compared to a standard concentration curve derived from a known concentration of bovine serum albumin.

Example 7

In this example, in vivo activity of functionalized microbubble embodiments is evaluated. tPA-functionalized microbubbles are used in a rat hindlimb model of microvascular obstruction. This model can be used to provide an accessible vascular bed that can be imaged. The following samples are evaluated with the model: (1) full systemic dose tPA (no ultrasound; no microbubble); (2) tPA-functionalized microbubble+UTMC; (3) pre-burst tPA-functionalized microbubbles+UTMC; (4) non-functionalized microbubbles+UTMC. Ultrasound parameters disclosed herein are used and in some embodiments, the ultrasound parameters yielding the greatest reperfusion in vitro, as measured by the pressure vs time curve, are used. Sample groups 2 and 3 are compared to evaluate the efficacy of targeted (that is, tPA attached to a microbubble) vs systemic delivery of identical tPA doses. Tissue is assessed for ROS, NO, gene expression, and lactate. The access site and postmortem brain tissue are analyzed for bleeding.

Sonoreperfusion efficacy is evaluated from video intensity vs time data measured from CEUS perfusion images of the hindlimb microcirculation. Some embodiments can provide ≥80% recovery of microvascular blood volume compared to baseline. Sonoreperfusion with tPA-functionalized microbubbles can yield (i) non-inferior reperfusion as compared to a full systemic tPA alone, with less bleeding; (ii) synergistically superior reperfusion for a given ultrasound energy compared to non-functionalized microbubbles; and/or (iii) greater reperfusion vs pre-burst tPA-functionalized microbubbles, due to targeted delivery. tPA and D-dimer levels are assessed using ELISA methods to show that tPA-functionalized microbubbles do not cause a systemic lytic state. Lower tissue ROS, greater muscle NO, and increased vasculo/cytoprotective gene expression can be observed when sonoreperfusion is used with tPA-functionalized microbubbles as compared to non-functionalized microbubbles.

In view of the many possible embodiments to which the principles of the present disclosure may be applied, it should be recognized that the illustrated embodiments are only examples and should not be taken as limiting scope. Rather, the scope of the present disclosure is defined by the following claims. We therefore claim as our invention all that comes within the scope and spirit of these claims.

We claim:

1. A functionalized microbubble, comprising:
   a microbubble comprising a lipid-based shell, wherein the lipid-based shell comprises (i) an interior circumferential region that defines a core of the microbubble and (ii) an exterior circumferential region; and
   at least one exteriorly-positioned thrombolytic agent attached to the exterior circumferential region of the lipid-based shell; wherein the at least one exteriorly-positioned thrombolytic agent extends from the exterior circumferential region and away from the core and is directly or indirectly attached to the exterior circumferential region of the lipid-based shell by a covalent bond or a specific binding interaction.

2. The functionalized microbubble of claim 1, wherein the lipid-based shell comprises a single layer of a plurality of lipid species and wherein one or more of the lipid species of the plurality comprises a first member of a specific binding pair; a linker group comprising an aliphatic group, a heteroaliphatic group, an aromatic group, an organic functional group, or any combination thereof; a covalent binding partner group selected from a carboxylic acid group, a carbodiimide-modified carboxylic acid group, or a maleimide group; or any combination thereof.

3. The functionalized microbubble of claim 2, wherein the first member of the specific binding pair member is biotin, streptavidin, avidin, or a deglycosylated avidin.

4. The functionalized microbubble of claim 1, wherein the exteriorly-positioned thrombolytic agent comprises a covalent binding partner group selected from an amine or a thiol group; a second member of a specific binding pair; a linker group; or a combination thereof.

5. The functionalized microbubble of claim 1, wherein the exteriorly-positioned thrombolytic agent is a tissue plasminogen activator.

6. The functionalized microbubble of claim 1, wherein the exteriorly-positioned thrombolytic agent is a tissue plasminogen activator and is covalently attached to at least one lipid of the lipid-based shell or is attached to at least one lipid of the lipid-based shell through the specific binding interaction.

7. The functionalized microbubble of claim 1, wherein the exteriorly-positioned thrombolytic agent is encapsulated in a liposome and the liposome is directly attached to the exterior circumferential region of the lipid-based shell.

8. The functionalized microbubble of claim 7, wherein the liposome is covalently attached to at least one lipid of the lipid-based shell or is attached to at least one lipid of the lipid-based shell through the specific binding interaction.

9. The functionalized microbubble of claim 1, comprising an amount of the exteriorly-positioned thrombolytic agent ranging from $1\ e^{-7}$ μg to $7\ e^{-7}$ μg.

10. The functionalized microbubble of claim 1, further comprising an additional therapeutically active agent, a visualization agent, a targeting agent, or any combination thereof that is (i) attached to the exterior circumferential region of the lipid-based shell; or (ii) is embedded in the lipid-based shell; or (iii) is located in the core of the microbubble; or (iv) any two or more of (i), (ii), and (iii).

11. The functionalized microbubble of claim 10, wherein the additional therapeutically active agent is an anticancer agent, a gene, a protein, or an antiplatelet drug; the visualization agent is a contrast agent, a fluorophore, a quantum dot, or a dye; and/or the targeting agent is p-selectin.

12. A method, comprising:
    exposing a subject in need of or a sample to the functionalized microbubble of claim 1, or a therapeutic composition thereof; and
    applying an ultrasound tone burst within a vicinity of the functionalized microbubble.

13. The method of claim 12, comprising exposing a subject to the functionalized microbubble or the therapeutic composition by administering the functionalized microbubble or the therapeutic composition via intravenous injection.

14. The method of claim 13, wherein the intravenous injection is into a microvessel comprising a thrombus or other microvascular obstruction.

15. The method of claim 13, wherein the ultrasound tone burst is sufficiently energetic so as to cause disruption of the functionalized microbubble by disrupting the lipid-based shell, releasing the exteriorly-positioned thrombolytic agent from the lipid-based shell, or a combination thereof.

16. The method of claim 13, wherein the ultrasound tone burst is an ultrasound tone burst of greater than 5 acoustic cycles with both (i) a pulse repetition frequency of between 0.01 and 20 Hz; and (ii) a pressure amplitude of greater than 0.3 MPa.

17. The method of claim 13, wherein the ultrasound tone burst is an ultrasound tone burst comprising 5000 cycles at 1 MHz, with both a pulse repetition frequency of 0.33 Hz and applying a pressure amplitude of 1.5 Mpa; an ultrasound tone burst comprising 1000 cycles at 1 MHz, with both a pulse repetition frequency of 0.33 Hz and applying a pressure amplitude of 1.0 Mpa;
    ultrasound tone burst comprising 500 cycles at 1 MHz, with both a pulse repetition frequency of 0.33 Hz and applying a pressure amplitude of 0.75 Mpa; or any combination thereof.

18. The method of claim 13, further comprising visually detecting the microbubble in the subject or the sample by detecting microbubble inertial cavitation after exposing applying the ultrasound tone burst.

19. The method of claim 13, wherein the method is used to treat or prevent strokes, peripheral vascular disease, ischemia, aneurysms, pulmonary embolism, sickle cell anemia, or any other disease caused by or involving blood clots or other vascular obstructions.

20. A method for treating a microvascular obstruction in a microvascular structure, comprising:
  exposing a subject in need of or a sample to the functionalized microbubble of claim 1, or a therapeutic composition thereof;
  visualizing the functionalized microbubble in the subject or the sample after exposure;
  applying one or more tone bursts of ultrasound within a vicinity of the functionalized microbubble once the functionalized microbubble is in proximity of a thrombus; and
  reducing a size of the thrombus to a size sufficient to remove the microvascular obstruction and allow blood flow to continue through the microvascular structure.

21. A therapeutic composition, comprising:
  a microbubble functionalized with an exteriorly-positioned thrombolytic agent that is directly or indirectly attached to the microbubble by a covalent bond or a specific binding interaction; and
  a pharmaceutically acceptable excipient, one or more additional therapeutically active agents or visualization agents, or any combinations thereof.

22. The therapeutic composition of claim 21, further comprising a microbubble that is not functionalized with the exteriorly-positioned thrombolytic agent.

* * * * *